United States Patent
Carson

(10) Patent No.: US 8,109,942 B2
(45) Date of Patent: Feb. 7, 2012

(54) COMPUTER-AIDED METHODS, SYSTEMS, AND APPARATUSES FOR SHOULDER ARTHROPLASTY

(75) Inventor: Christopher Patrick Carson, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1789 days.

(21) Appl. No.: 11/111,325

(22) Filed: Apr. 21, 2005

(65) Prior Publication Data
US 2005/0245808 A1 Nov. 3, 2005

Related U.S. Application Data

(60) Provisional application No. 60/564,162, filed on Apr. 21, 2004.

(51) Int. Cl.
*A61B 19/00* (2006.01)
(52) U.S. Cl. .................................................... 606/130
(58) Field of Classification Search .................. 606/130, 606/87, 86 R, 79, 80, 96; 600/429, 439, 600/424, 426, 407, 443
See application file for complete search history.

(56) References Cited

U.S. PATENT DOCUMENTS

| | | |
|---|---|---|
| 100,602 A | 3/1870 | Coes |
| 1,076,971 A | 10/1913 | Geiger |
| 1,201,467 A | 10/1916 | Hoglund |
| 2,092,869 A | 9/1937 | Baum |
| 3,412,733 A | 11/1968 | Ross |
| 3,457,922 A | 7/1969 | Ray |
| 3,702,611 A | 11/1972 | Fishbein |
| 4,305,394 A | 12/1981 | Bertuch, Jr. |
| 4,323,080 A | 4/1982 | Melharty |
| 4,421,112 A | 12/1983 | Mains et al. |
| 4,456,010 A | 6/1984 | Reimels et al. |
| 4,457,307 A | 7/1984 | Stillwell |
| 4,483,554 A | 11/1984 | Ernst |
| 4,524,766 A | 6/1985 | Petersen |

(Continued)

FOREIGN PATENT DOCUMENTS

DE 042 25 112 C 12/1993

(Continued)

OTHER PUBLICATIONS

English-language abstract of CN 101224104 published on Jul. 23, 2008, Quan, Renfu, et al., Inventors.

(Continued)

*Primary Examiner* — Gary Jackson
*Assistant Examiner* — Michael G Mendoza
(74) *Attorney, Agent, or Firm* — Krieg DeVault LLP

(57) ABSTRACT

A method for performing shoulder arthroplasty or hemiarthroplasty is provided. The method includes generating navigational reference information relating to position and orientation of a body part forming at least a portion of the shoulder joint. The reference information may be stored in a computer. Navigational references are attached to the body part and an object. Information is received regarding the position and orientation of the object with respect to the body part and the object is navigated according to this information. The body part may be modified using the object and the modification may be displayed on a monitor associated with the computer. The navigational references may be used to track a shoulder arthroplasty trial component. Information is received regarding the position and orientation of the trial component with respect to the body part. This information is used to navigate the trial component to the body part.

26 Claims, 8 Drawing Sheets

U.S. PATENT DOCUMENTS

| | | |
|---|---|---|
| 4,534,364 A | 8/1985 | Lamoreux |
| 4,565,192 A | 1/1986 | Shapiro |
| 4,566,448 A | 1/1986 | Rohr, Jr. |
| 4,567,885 A | 2/1986 | Androphy |
| 4,567,886 A | 2/1986 | Petersen |
| 4,574,794 A | 3/1986 | Cooke et al. |
| 4,583,554 A | 4/1986 | Mittelman et al. |
| 4,671,275 A | 6/1987 | Deyerle |
| 4,703,751 A | 11/1987 | Pohl |
| 4,712,951 A | 12/1987 | Brown |
| 4,718,413 A | 1/1988 | Johnson |
| 4,722,056 A | 1/1988 | Roberts et al. |
| 4,738,256 A | 4/1988 | Freeman et al. |
| 4,759,350 A | 7/1988 | Dunn et al. |
| 4,768,504 A | 9/1988 | Ender |
| 4,777,942 A | 10/1988 | Frey et al. |
| 4,802,468 A | 2/1989 | Powlan |
| 4,803,976 A | 2/1989 | Frigg et al. |
| 4,809,689 A | 3/1989 | Anapliotis |
| 4,815,899 A | 3/1989 | Regan |
| 4,875,475 A | 10/1989 | Comte et al. |
| 4,892,093 A | 1/1990 | Zarnowski et al. |
| 4,913,163 A | 4/1990 | Roger et al. |
| 4,938,762 A | 7/1990 | Wehrli |
| 4,952,213 A | 8/1990 | Bowman et al. |
| 4,964,862 A | 10/1990 | Arms |
| 4,991,579 A | 2/1991 | Allen |
| 5,002,545 A | 3/1991 | Whiteside et al. |
| 5,002,578 A | 3/1991 | Luman |
| 5,016,639 A | 5/1991 | Allen |
| 5,037,423 A | 8/1991 | Kenna |
| 5,037,426 A | 8/1991 | Goble et al. |
| 5,049,149 A | 9/1991 | Schmidt |
| 5,053,039 A | 10/1991 | Hofmann et al. |
| 5,078,719 A | 1/1992 | Schreiber |
| 5,092,869 A | 3/1992 | Waldron |
| 5,094,241 A | 3/1992 | Allen |
| 5,097,839 A | 3/1992 | Allen |
| 5,098,426 A | 3/1992 | Sklar et al. |
| 5,116,338 A | 5/1992 | Poggie et al. |
| 5,119,817 A | 6/1992 | Allen |
| 5,122,144 A | 6/1992 | Bert et al. |
| 5,129,909 A | 7/1992 | Sutherland |
| 5,147,408 A | 9/1992 | Noble |
| 5,190,547 A | 3/1993 | Barber, Jr. et al. |
| 5,211,164 A | 5/1993 | Allen |
| 5,213,312 A | 5/1993 | MacDonald |
| 5,217,499 A | 6/1993 | Shelley |
| 5,230,338 A | 7/1993 | Allen et al. |
| 5,246,444 A | 9/1993 | Schreiber |
| 5,254,119 A | 10/1993 | Schreiber |
| 5,263,972 A | 11/1993 | Evans et al. |
| 5,289,826 A | 3/1994 | Kovacevic |
| 5,305,203 A | 4/1994 | Raab |
| 5,342,366 A | 8/1994 | Whiteside et al. |
| 5,360,016 A | 11/1994 | Kovacevic |
| 5,364,401 A | 11/1994 | Ferrante et al. |
| 5,364,402 A | 11/1994 | Mumme et al. |
| 5,365,996 A | 11/1994 | Crook |
| 5,375,588 A | 12/1994 | Yoon |
| 5,379,133 A | 1/1995 | Kirk |
| 5,383,454 A | 1/1995 | Bucholz |
| 5,387,218 A | 2/1995 | Meswania et al. |
| 5,389,101 A | 2/1995 | Heilbrun et al. |
| 5,395,376 A | 3/1995 | Caspari et al. |
| 5,397,329 A | 3/1995 | Allen |
| 5,403,320 A | 4/1995 | Luman |
| 5,423,828 A | 6/1995 | Benson |
| 5,425,355 A | 6/1995 | Kulick |
| 5,445,166 A | 8/1995 | Taylor |
| 5,445,642 A | 8/1995 | McNulty et al. |
| 5,449,360 A | 9/1995 | Schreiber |
| 5,452,407 A | 9/1995 | Crook |
| 5,462,548 A | 10/1995 | Pappas et al. |
| 5,462,549 A | 10/1995 | Glock |
| 5,468,244 A | 11/1995 | Attfield et al. |
| 5,470,354 A | 11/1995 | Hershberger et al. |
| 5,474,559 A | 12/1995 | Bertin et al. |
| 5,484,437 A | 1/1996 | Michelson |
| 5,486,178 A | 1/1996 | Hodge |
| 5,490,854 A | 2/1996 | Fisher et al. |
| 5,491,510 A | 2/1996 | Gove |
| 5,507,824 A | 4/1996 | Lennox |
| 5,514,139 A | 5/1996 | Goldstein et al. |
| 5,517,990 A | 5/1996 | Kalfas et al. |
| 5,527,316 A | 6/1996 | Williamson |
| 5,540,691 A | 7/1996 | Elstrom et al. |
| 5,540,694 A | 7/1996 | DeCarlo, Jr. |
| 5,540,695 A | 7/1996 | Levy |
| 5,540,696 A | 7/1996 | Booth, Jr. et al. |
| 5,569,260 A | 10/1996 | Petersen |
| 5,597,379 A | 1/1997 | Haines et al. |
| 5,598,269 A | 1/1997 | Kitaevich et al. |
| 5,603,318 A | 2/1997 | Heilbrun et al. |
| 5,613,969 A | 3/1997 | Jenkins, Jr. |
| 5,643,268 A | 7/1997 | Vilsmeier et al. |
| 5,643,272 A | 7/1997 | Haines et al. |
| 5,658,290 A | 8/1997 | Lechot |
| 5,669,914 A | 9/1997 | Eckhoff |
| 5,676,668 A | 10/1997 | McCue et al. |
| 5,681,316 A | 10/1997 | DeOrio et al. |
| 5,682,886 A | 11/1997 | Delp et al. |
| 5,683,397 A | 11/1997 | Vendrely et al. |
| 5,688,279 A | 11/1997 | McNulty et al. |
| 5,693,056 A | 12/1997 | Carls et al. |
| 5,695,501 A | 12/1997 | Carol et al. |
| 5,702,406 A | 12/1997 | Vilsmeier et al. |
| 5,704,941 A | 1/1998 | Jacober et al. |
| 5,707,370 A | 1/1998 | Berki et al. |
| 5,709,689 A | 1/1998 | Ferrante et al. |
| 5,715,836 A | 2/1998 | Kliegis et al. |
| 5,716,361 A | 2/1998 | Masini |
| 5,720,752 A | 2/1998 | Elliott et al. |
| 5,722,978 A | 3/1998 | Jenkins, Jr. |
| 5,727,554 A | 3/1998 | Kalend et al. |
| 5,733,292 A | 3/1998 | Gustilo et al. |
| 5,735,904 A | 4/1998 | Pappas |
| 5,743,915 A | 4/1998 | Bertin et al. |
| 5,748,767 A | 5/1998 | Raab |
| 5,755,725 A | 5/1998 | Druais |
| 5,755,803 A | 5/1998 | Haines et al. |
| 5,769,861 A | 6/1998 | Vilsmeier |
| 5,772,593 A | 6/1998 | Hakamata |
| 5,772,594 A | 6/1998 | Barrick |
| 5,776,064 A | 7/1998 | Kalfas et al. |
| 5,782,842 A | 7/1998 | Kloess et al. |
| 5,792,147 A | 8/1998 | Evans et al. |
| 5,797,924 A | 8/1998 | Schulte et al. |
| 5,799,055 A | 8/1998 | Peshkin et al. |
| 5,800,352 A | 9/1998 | Ferre et al. |
| 5,800,438 A | 9/1998 | Tuke et al. |
| 5,806,518 A * | 9/1998 | Mittelstadt .................... 600/407 |
| 5,807,252 A | 9/1998 | Hassfeld et al. |
| 5,810,827 A | 9/1998 | Haines et al. |
| 5,810,841 A | 9/1998 | McNeirney et al. |
| 5,817,097 A | 10/1998 | Howard et al. |
| 5,830,214 A | 11/1998 | Flom et al. |
| 5,836,954 A | 11/1998 | Heilbrun et al. |
| 5,848,967 A | 12/1998 | Cosman |
| 5,850,836 A | 12/1998 | Steiger et al. |
| 5,860,981 A | 1/1999 | Bertin et al. |
| 5,865,809 A | 2/1999 | Moenning et al. |
| 5,871,018 A | 2/1999 | Delp et al. |
| 5,871,445 A | 2/1999 | Bucholz |
| 5,873,822 A | 2/1999 | Ferre et al. |
| 5,879,352 A | 3/1999 | Filoso et al. |
| 5,879,354 A | 3/1999 | Haines et al. |
| 5,880,976 A | 3/1999 | DiGioia, III et al. |
| 5,885,296 A | 3/1999 | Masini |
| 5,885,297 A | 3/1999 | Matsen, III |
| 5,897,559 A | 4/1999 | Masinie |
| 5,916,221 A | 6/1999 | Hodorek et al. |
| 5,920,395 A | 7/1999 | Schulz |
| 5,921,992 A | 7/1999 | Costales et al. |
| 5,925,049 A | 7/1999 | Gustilo et al. |
| 5,935,128 A | 8/1999 | Carter et al. |
| 5,938,665 A | 8/1999 | Martin |

| | | |
|---|---|---|
| 5,944,722 A | 8/1999 | Masini |
| 5,947,971 A | 9/1999 | Kuslich et al. |
| 5,947,973 A | 9/1999 | Masini |
| 5,951,561 A | 9/1999 | Pepper et al. |
| 5,957,926 A | 9/1999 | Masini |
| 5,961,523 A | 10/1999 | Masini |
| 5,971,989 A | 10/1999 | Masini |
| 5,980,526 A | 11/1999 | Johnson et al. |
| 5,980,535 A | 11/1999 | Barnett et al. |
| 5,999,837 A | 12/1999 | Messner et al. |
| 6,001,106 A | 12/1999 | Ryan et al. |
| 6,002,859 A | 12/1999 | DiGioia, III et al. |
| 6,006,126 A | 12/1999 | Cosman |
| 6,006,127 A | 12/1999 | Van Der Brug et al. |
| 6,007,537 A | 12/1999 | Burkinshaw et al. |
| 6,010,506 A | 1/2000 | Gosney et al. |
| 6,011,987 A | 1/2000 | Barnett |
| 6,016,606 A | 1/2000 | Oliver et al. |
| 6,021,342 A | 2/2000 | Brabrand |
| 6,021,343 A | 2/2000 | Foley et al. |
| 6,022,377 A | 2/2000 | Nuelle et al. |
| 6,026,315 A | 2/2000 | Lenz et al. |
| 6,030,391 A | 2/2000 | Brainard et al. |
| 6,033,410 A | 3/2000 | McLean et al. |
| 6,041,249 A | 3/2000 | Regn |
| 6,044,291 A | 3/2000 | Rockseisen |
| 6,045,556 A | 4/2000 | Cohen |
| 6,050,724 A | 4/2000 | Schmitz et al. |
| 6,053,922 A | 4/2000 | Krause et al. |
| 6,056,756 A | 5/2000 | Eng et al. |
| 6,068,633 A | 5/2000 | Masini |
| 6,069,932 A | 5/2000 | Peshkin et al. |
| 6,073,044 A | 6/2000 | Fitzpatrick et al. |
| 6,077,269 A | 6/2000 | Masini |
| 6,081,336 A | 6/2000 | Messner et al. |
| 6,083,163 A | 7/2000 | Wegner et al. |
| 6,096,048 A | 8/2000 | Howard et al. |
| 6,102,916 A | 8/2000 | Masini |
| 6,132,433 A | 10/2000 | Whelan |
| 6,143,390 A | 11/2000 | Takamiya et al. |
| 6,144,875 A | 11/2000 | Schweikard et al. |
| 6,146,390 A | 11/2000 | Heilbrun et al. |
| 6,148,280 A | 11/2000 | Kramer |
| 6,161,033 A | 12/2000 | Kuhn |
| 6,162,190 A | 12/2000 | Kramer |
| 6,165,181 A | 12/2000 | Heilbrun et al. |
| 6,167,145 A | 12/2000 | Foley et al. |
| 6,167,292 A | 12/2000 | Badano et al. |
| 6,167,295 A | 12/2000 | Cosman |
| 6,167,296 A | 12/2000 | Shahidi |
| 6,168,627 B1 | 1/2001 | Huebner |
| 6,174,335 B1 | 1/2001 | Varieur |
| 6,185,315 B1 | 2/2001 | Schmucker et al. |
| 6,187,010 B1 | 2/2001 | Masini |
| 6,190,320 B1 | 2/2001 | Lelong |
| 6,190,395 B1 | 2/2001 | Williams |
| 6,195,168 B1 | 2/2001 | De Lega et al. |
| 6,197,064 B1 | 3/2001 | Haines et al. |
| 6,198,794 B1 | 3/2001 | Peshkin et al. |
| 6,200,316 B1 | 3/2001 | Zwirkoski et al. |
| 6,205,411 B1 | 3/2001 | DiGioia, III et al. |
| 6,211,976 B1 | 4/2001 | Popovich et al. |
| 6,214,011 B1 | 4/2001 | Masini |
| 6,216,029 B1 | 4/2001 | Paltieli |
| 6,223,067 B1 | 4/2001 | Vilsmeier et al. |
| 6,226,548 B1 | 5/2001 | Foley et al. |
| 6,228,090 B1 | 5/2001 | Waddell |
| 6,228,092 B1 | 5/2001 | Mikhail |
| 6,235,038 B1 | 5/2001 | Hunter et al. |
| 6,236,875 B1 | 5/2001 | Bucholz et al. |
| 6,241,735 B1 | 6/2001 | Marmulla |
| 6,249,581 B1 | 6/2001 | Kok |
| 6,258,095 B1 | 7/2001 | Lombardo et al. |
| 6,258,096 B1 | 7/2001 | Seki |
| 6,264,647 B1 | 7/2001 | Lechot |
| 6,283,971 B1 | 9/2001 | Temeles |
| 6,285,902 B1 | 9/2001 | Kienzle, III et al. |
| 6,295,513 B1 | 9/2001 | Thackston |
| 6,317,616 B1 | 11/2001 | Glossop |
| 6,319,256 B1 | 11/2001 | Spotorno |
| 6,332,891 B1 | 12/2001 | Himes |
| 6,333,971 B2 | 12/2001 | McCrory et al. |
| 6,344,853 B1 | 2/2002 | Knight |
| 6,347,240 B1 | 2/2002 | Foley et al. |
| 6,351,659 B1 | 2/2002 | Vilsmeier |
| 6,351,661 B1 | 2/2002 | Cosman |
| 6,377,839 B1 | 4/2002 | Kalfas et al. |
| 6,383,188 B2 | 5/2002 | Kuslich et al. |
| 6,385,475 B1 | 5/2002 | Cinquin et al. |
| 6,405,072 B1 | 6/2002 | Cosman |
| 6,413,261 B1 | 7/2002 | Grundei |
| 6,434,507 B1 | 8/2002 | Clayton et al. |
| 6,440,140 B2 | 8/2002 | Bullivant et al. |
| 6,443,956 B1 | 9/2002 | Ray |
| 6,451,059 B1 | 9/2002 | Janas et al. |
| 6,458,135 B1 | 10/2002 | Harwin et al. |
| 6,463,351 B1 | 10/2002 | Clynch |
| 6,468,202 B1 | 10/2002 | Irion et al. |
| 6,477,400 B1 | 11/2002 | Barrick |
| 6,478,799 B1 | 11/2002 | Williamson |
| 6,484,049 B1 | 11/2002 | Seeley et al. |
| 6,490,467 B1 | 12/2002 | Bucholz et al. |
| 6,491,429 B1 | 12/2002 | Suhm |
| 6,491,702 B2 | 12/2002 | Heilbrun et al. |
| 6,503,249 B1 | 1/2003 | Krause |
| 6,503,254 B2 | 1/2003 | Masini |
| 6,527,443 B1 | 3/2003 | Vilsmeier et al. |
| 6,540,739 B2 | 4/2003 | Lechot |
| 6,546,279 B1 | 4/2003 | Bova et al. |
| 6,551,319 B2 | 4/2003 | Lieberman |
| 6,551,324 B2 | 4/2003 | Muller |
| 6,551,325 B2 | 4/2003 | Neubauer et al. |
| 6,554,837 B1 | 4/2003 | Hauri et al. |
| 6,558,391 B2 | 5/2003 | Axelson, Jr. et al. |
| 6,558,421 B1 | 5/2003 | Fell et al. |
| 6,567,687 B2 | 5/2003 | Front et al. |
| 6,574,493 B2 | 6/2003 | Rasche et al. |
| 6,589,248 B1 * | 7/2003 | Hughes ............... 606/102 |
| 6,595,997 B2 | 7/2003 | Axelson, Jr. et al. |
| 6,602,259 B1 | 8/2003 | Masini |
| 6,620,168 B1 | 9/2003 | Lombardo et al. |
| 6,620,268 B2 | 9/2003 | Cho et al. |
| 6,640,127 B1 | 10/2003 | Kosaka et al. |
| 6,652,142 B2 | 11/2003 | Launay et al. |
| 6,662,036 B2 | 12/2003 | Cosman |
| 6,673,077 B1 | 1/2004 | Katz |
| 6,675,040 B1 | 1/2004 | Cosman |
| 6,685,711 B2 | 2/2004 | Axelson, Jr. et al. |
| 6,690,964 B2 | 2/2004 | Bieger et al. |
| 6,692,447 B1 | 2/2004 | Picard |
| 6,694,168 B2 | 2/2004 | Traxel et al. |
| 6,695,848 B2 | 2/2004 | Haines |
| 6,702,821 B2 | 3/2004 | Bonutti |
| 6,711,431 B2 | 3/2004 | Sarin et al. |
| 6,712,823 B2 | 3/2004 | Grusin et al. |
| 6,712,824 B2 | 3/2004 | Millard et al. |
| 6,716,249 B2 | 4/2004 | Hyde |
| 6,718,194 B2 | 4/2004 | Kienzle |
| 6,725,080 B2 | 4/2004 | Melkent et al. |
| 6,725,082 B2 | 4/2004 | Sati et al. |
| 6,728,599 B2 | 4/2004 | Wright et al. |
| 6,772,026 B2 | 8/2004 | Bradbury et al. |
| 6,780,190 B2 | 8/2004 | Maroney |
| 6,785,593 B2 | 8/2004 | Wang |
| 6,799,088 B2 | 9/2004 | Wang |
| 6,814,490 B1 | 11/2004 | Suhm et al. |
| 6,827,723 B2 | 12/2004 | Carson |
| 6,836,703 B2 | 12/2004 | Wang |
| 6,871,117 B2 | 3/2005 | Wang |
| 6,882,982 B2 | 4/2005 | McMenimen |
| 6,892,112 B2 | 5/2005 | Wang |
| 6,905,514 B2 | 6/2005 | Carignan et al. |
| 6,923,817 B2 | 8/2005 | Carson |
| 6,947,786 B2 | 9/2005 | Simon et al. |
| 6,993,374 B2 | 1/2006 | Sasso |
| 7,001,346 B2 | 2/2006 | White |
| 7,035,702 B2 | 4/2006 | Jelonek et al. |
| 7,237,556 B2 | 7/2007 | Smothers |

| | | |
|---|---|---|
| 7,241,298 B2 | 7/2007 | Nemec et al. |
| 2001/0001120 A1 | 5/2001 | Masini |
| 2001/0010004 A1 | 7/2001 | Traxel et al. |
| 2001/0014772 A1 | 8/2001 | Lampotang et al. |
| 2001/0016745 A1 | 8/2001 | Bullivant et al. |
| 2001/0034530 A1 | 10/2001 | Malackowski et al. |
| 2001/0036245 A1 | 11/2001 | Kienzle, III et al. |
| 2001/0039421 A1 | 11/2001 | Heilbrun et al. |
| 2002/0002330 A1 | 1/2002 | Vilsmeier |
| 2002/0002365 A1 | 1/2002 | Lechot |
| 2002/0007294 A1 | 1/2002 | Bradbury et al. |
| 2002/0011594 A1 | 1/2002 | DeSouza |
| 2002/0016540 A1 | 2/2002 | Mikus et al. |
| 2002/0018981 A1 | 2/2002 | Andersson et al. |
| 2002/0029041 A1 | 3/2002 | Hover et al. |
| 2002/0032451 A1 | 3/2002 | Tierney et al. |
| 2002/0038085 A1 | 3/2002 | Immerz |
| 2002/0052606 A1 | 5/2002 | Bonutti |
| 2002/0065461 A1 | 5/2002 | Cosman |
| 2002/0068942 A1 | 6/2002 | Neubauer et al. |
| 2002/0072748 A1 | 6/2002 | Robioneck |
| 2002/0072821 A1 | 6/2002 | Baker |
| 2002/0077533 A1 | 6/2002 | Bieger et al. |
| 2002/0077540 A1 | 6/2002 | Kienzle, III |
| 2002/0085681 A1 | 7/2002 | Jensen |
| 2002/0087101 A1 | 7/2002 | Barrick et al. |
| 2002/0095081 A1 | 7/2002 | Vilsmeier |
| 2002/0102214 A1 | 8/2002 | Briley-Saebo et al. |
| 2002/0107518 A1 | 8/2002 | Neubauer et al. |
| 2002/0115934 A1 | 8/2002 | Tuke |
| 2002/0133161 A1 | 9/2002 | Axelson et al. |
| 2002/0133175 A1 | 9/2002 | Carson |
| 2002/0147455 A1 | 10/2002 | Carson |
| 2002/0151894 A1 | 10/2002 | Melkent et al. |
| 2002/0151898 A1 | 10/2002 | Sohngen et al. |
| 2002/0156371 A1 | 10/2002 | Hedlund et al. |
| 2002/0156479 A1 | 10/2002 | Schulzki et al. |
| 2002/0188194 A1 | 12/2002 | Cosman |
| 2002/0193800 A1 | 12/2002 | Kienzle, III et al. |
| 2002/0198448 A1 | 12/2002 | Zuk et al. |
| 2002/0198451 A1 | 12/2002 | Carson |
| 2002/0198531 A1 | 12/2002 | Millard et al. |
| 2003/0018338 A1 | 1/2003 | Axelson, Jr. et al. |
| 2003/0045883 A1 | 3/2003 | Chow et al. |
| 2003/0050643 A1 | 3/2003 | Taft |
| 2003/0065400 A1 | 4/2003 | Bradbury |
| 2003/0069591 A1 | 4/2003 | Carson et al. |
| 2003/0073901 A1 | 4/2003 | Simon et al. |
| 2003/0153829 A1 | 8/2003 | Sarin et al. |
| 2003/0153859 A1 | 8/2003 | Hinshon |
| 2003/0153978 A1 | 8/2003 | Whiteside |
| 2003/0164172 A1 | 9/2003 | Chumas et al. |
| 2003/0181918 A1 | 9/2003 | Smothers et al. |
| 2003/0187351 A1 | 10/2003 | Franck et al. |
| 2003/0187452 A1 | 10/2003 | Smith et al. |
| 2003/0192557 A1 | 10/2003 | Krag et al. |
| 2003/0225329 A1 | 12/2003 | Rossner et al. |
| 2004/0019382 A1 | 1/2004 | Amirouche et al. |
| 2004/0030237 A1 | 2/2004 | Lee et al. |
| 2004/0030245 A1 | 2/2004 | Noble et al. |
| 2004/0039396 A1 | 2/2004 | Couture et al. |
| 2004/0054489 A1 | 3/2004 | Moctezuma De La Barrera |
| 2004/0073279 A1 | 4/2004 | Malackowski et al. |
| 2004/0087852 A1 | 5/2004 | Chen et al. |
| 2004/0092944 A1 | 5/2004 | Penenberg |
| 2004/0097952 A1 | 5/2004 | Sarin et al. |
| 2004/0152955 A1 | 8/2004 | McGinley et al. |
| 2004/0152970 A1 | 8/2004 | Hunter et al. |
| 2004/0152972 A1 | 8/2004 | Hunter |
| 2004/0153081 A1 | 8/2004 | Tulkis |
| 2004/0153083 A1 | 8/2004 | Nemec et al. |
| 2004/0167391 A1 | 8/2004 | Solar et al. |
| 2004/0169673 A1 | 9/2004 | Crampe et al. |
| 2004/0171924 A1 | 9/2004 | Mire et al. |
| 2004/0243481 A1 | 12/2004 | Bradbury et al. |
| 2004/0254586 A1 | 12/2004 | Sarin |
| 2004/0260290 A1 | 12/2004 | Zander et al. |
| 2005/0021037 A1 | 1/2005 | McCombs et al. |
| 2005/0021043 A1 | 1/2005 | Jansen |
| 2005/0075632 A1 | 4/2005 | Russell et al. |
| 2005/0085715 A1 | 4/2005 | Dukesherer et al. |
| 2005/0085822 A1 | 4/2005 | Thornberry et al. |
| 2005/0101966 A1 | 5/2005 | Lavailee |
| 2005/0109855 A1 | 5/2005 | McCombs |
| 2005/0113658 A1 | 5/2005 | Jacobson et al. |
| 2005/0113659 A1 | 5/2005 | Pothier |
| 2005/0113846 A1 | 5/2005 | Carson |
| 2005/0119639 A1 | 6/2005 | McCombs |
| 2005/0119661 A1 | 6/2005 | Hodgson et al. |
| 2005/0119777 A1 | 6/2005 | Arbogast et al. |
| 2005/0124988 A1 | 6/2005 | Terrill-Grisoni et al. |
| 2005/0148843 A1 | 7/2005 | Roose |
| 2005/0149003 A1 | 7/2005 | Tierney et al. |
| 2005/0149041 A1 | 7/2005 | McGinley |
| 2005/0154331 A1 | 7/2005 | Christie et al. |
| 2005/0159759 A1 | 7/2005 | Harbaugh et al. |
| 2005/0177172 A1 | 8/2005 | Acker |
| 2005/0197569 A1 | 9/2005 | McCombs |
| 2005/0197814 A1 | 9/2005 | Aram et al. |
| 2005/0203384 A1 | 9/2005 | Sati et al. |
| 2005/0209726 A1 | 9/2005 | Voit et al. |
| 2005/0216305 A1 | 9/2005 | Funderud |
| 2005/0228266 A1 | 10/2005 | McCombs |
| 2005/0228404 A1 | 10/2005 | Vandevelde |
| 2005/0234332 A1 | 10/2005 | Murphy |
| 2005/0234465 A1 | 10/2005 | McCombs |
| 2005/0234466 A1 | 10/2005 | Stallings |
| 2005/0234468 A1 | 10/2005 | Carson |
| 2005/0245808 A1 | 11/2005 | Carson |
| 2005/0279368 A1 | 12/2005 | McCombs |
| 2005/0288676 A1 | 12/2005 | Schnieders |
| 2006/0015120 A1 | 1/2006 | Richard et al. |
| 2006/0100504 A1 | 5/2006 | Jansen et al. |
| 2006/0161051 A1 | 7/2006 | Terrill-Grisoni et al. |
| 2006/0190011 A1 | 8/2006 | Ries |
| 2006/0200025 A1 | 9/2006 | Elliott |
| 2006/0229626 A1 | 10/2006 | Kelman |
| 2007/0118055 A1 | 5/2007 | McCombs |
| 2007/0123912 A1 | 5/2007 | Carson |
| 2007/0129629 A1 | 6/2007 | Beauregard et al. |
| 2007/0169782 A1 | 7/2007 | Castleman |
| 2008/0195109 A1 | 8/2008 | Hunter et al. |
| 2008/0269599 A1 | 10/2008 | Csavoy et al. |
| 2008/0269602 A1 | 10/2008 | Csavoy et al. |

FOREIGN PATENT DOCUMENTS

| | | |
|---|---|---|
| DE | 296 00 990 | 1/1996 |
| DE | 196 29 011 A1 | 1/1998 |
| DE | 197 09 960 A | 9/1998 |
| DE | 299 06 438 U1 | 9/1999 |
| DE | 296 23 941 U1 | 11/2000 |
| DE | 200 21 494 | 3/2001 |
| DE | 201 03 416 11 | 7/2001 |
| DE | 100 12 042 | 8/2001 |
| DE | 100 31 887 A1 | 1/2002 |
| DE | 102 07 035 | 2/2002 |
| DE | 100 45 381 A1 | 4/2002 |
| DE | 202 13 243 | 10/2002 |
| DE | 203 09 399 | 8/2003 |
| EP | 0 327 509 A1 | 8/1989 |
| EP | 0 327 509 B1 | 8/1989 |
| EP | 0 337 901 A1 | 10/1989 |
| EP | 0 340 176 A2 | 11/1989 |
| EP | 0 216 794 B1 | 12/1989 |
| EP | 0 366 488 B1 | 5/1990 |
| EP | 0 376 657 B1 | 7/1990 |
| EP | 0 380 451 A2 | 8/1990 |
| EP | 0 415 837 A2 | 3/1991 |
| EP | 0 466 659 A2 | 1/1992 |
| EP | 0 359 097 | 8/1992 |
| EP | 0 538 152 A1 | 4/1993 |
| EP | 0 538 153 B1 | 4/1993 |
| EP | 0 555 003 B1 | 8/1993 |
| EP | 0 428 303 | 7/1995 |
| EP | 0 676 178 A | 10/1995 |
| EP | 0 720 834 A2 | 7/1996 |
| EP | 0 619 097 | 6/1999 |
| EP | 1 149 562 A2 | 10/2001 |

| | | |
|---|---|---|
| EP | 1 033 108 | 2/2002 |
| EP | 1 190 676 B1 | 3/2002 |
| EP | 1 226 788 | 7/2002 |
| EP | 1 226 788 A1 | 7/2002 |
| EP | 0 782 842 | 9/2002 |
| EP | 1 236 450 A1 | 9/2002 |
| EP | 1 249 207 | 10/2002 |
| EP | 1 348 384 | 10/2003 |
| EP | 1 384 456 A2 | 1/2004 |
| EP | 1 405 603 A2 | 4/2004 |
| EP | 1 406 203 | 4/2004 |
| EP | 1 435 223 A1 | 7/2004 |
| EP | 1 442 715 | 8/2004 |
| EP | 1 459 686 A2 | 9/2004 |
| EP | 1 532 946 A2 | 5/2005 |
| EP | 1 563 795 | 8/2005 |
| FR | 2 828 397 | 2/2003 |
| GB | 2 224 937 | 5/1990 |
| GB | 2 397 769 A | 8/2004 |
| JP | 2002-304439 | 10/2002 |
| WO | WO 86/05384 | 9/1986 |
| WO | WO 89/09570 | 10/1989 |
| WO | WO 94/17733 | 8/1994 |
| WO | WO 95/15714 | 6/1995 |
| WO | WO 96/35387 | 11/1996 |
| WO | WO 97/16129 | 5/1997 |
| WO | WO 97/23172 | 7/1997 |
| WO | WO 97/29683 | 8/1997 |
| WO | WO 98/29032 | 7/1998 |
| WO | WO 98/46169 | 10/1998 |
| WO | WO 99/15097 | 4/1999 |
| WO | WO 99/27860 | 6/1999 |
| WO | WO 99/60939 | 12/1999 |
| WO | WO 99/65380 | 12/1999 |
| WO | WO 00/00093 | 1/2000 |
| WO | WO 00/21442 | 4/2000 |
| WO | WO 00/47103 | 8/2000 |
| WO | WO 0054687 | 9/2000 |
| WO | WO 00/64367 | 11/2000 |
| WO | WO 01/01845 A2 | 1/2001 |
| WO | WO 01/19271 A2 | 3/2001 |
| WO | WO 01/34050 A2 | 5/2001 |
| WO | WO 01/34050 A3 | 5/2001 |
| WO | WO2001043654 | 6/2001 |
| WO | WO 01/64124 A1 | 9/2001 |
| WO | WO 01/67979 A1 | 9/2001 |
| WO | WO 01/91647 A1 | 12/2001 |
| WO | WO 01/93770 A1 | 12/2001 |
| WO | WO 02/024096 A1 | 3/2002 |
| WO | WO 02/41794 A1 | 5/2002 |
| WO | WO 02/063236 A1 | 8/2002 |
| WO | WO 02/063236 A3 | 8/2002 |
| WO | WO 02/064042 | 8/2002 |
| WO | WO 02/067783 | 9/2002 |
| WO | WO 02/067784 | 9/2002 |
| WO | WO 02/067800 | 9/2002 |
| WO | WO 02/080824 A1 | 10/2002 |
| WO | 03/006107 | 1/2003 |
| WO | WO 03/006107 | 1/2003 |
| WO | WO 03/015642 | 2/2003 |
| WO | WO 03/030787 | 4/2003 |
| WO | WO 03/034213 A2 | 4/2003 |
| WO | WO 03/034933 A1 | 5/2003 |
| WO | WO 03/037192 A1 | 5/2003 |
| WO | WO 03/039377 | 5/2003 |
| WO | WO 03/041566 A2 | 5/2003 |
| WO | WO 03/065931 | 8/2003 |
| WO | WO 03/065949 A2 | 8/2003 |
| WO | WO 03/068090 A1 | 8/2003 |
| WO | WO 03/071969 A1 | 9/2003 |
| WO | WO 03/075740 A2 | 9/2003 |
| WO | WO 03/079940 | 10/2003 |
| WO | WO 03/096870 A2 | 11/2003 |
| WO | WO 2004/001569 A2 | 12/2003 |
| WO | WO 2004/017842 A2 | 3/2004 |
| WO | WO 2004/019792 | 3/2004 |
| WO | WO 2004/029908 A1 | 4/2004 |
| WO | WO 2004/030556 A2 | 4/2004 |
| WO | WO 2004/030559 A1 | 4/2004 |
| WO | WO 2004/046754 A2 | 6/2004 |
| WO | WO 2004/069036 | 8/2004 |
| WO | WO 2004/070580 | 8/2004 |
| WO | WO 2004/008740 A1 | 10/2004 |
| WO | WO 2004/084740 | 10/2004 |
| WO | WO 2004/001569 A2 | 12/2004 |
| WO | WO 2005/009303 A1 | 2/2005 |
| WO | WO 2005/039430 A2 | 5/2005 |
| WO | WO 2005/041802 A1 | 5/2005 |
| WO | WO 2005/044126 A1 | 5/2005 |
| WO | WO 2005/048851 A1 | 6/2005 |
| WO | WO 2005/053559 A1 | 6/2005 |
| WO | WO 2005/057439 | 6/2005 |
| WO | WO 2005/070312 A1 | 8/2005 |
| WO | WO 2005/070319 A1 | 8/2005 |
| WO | WO 2005/072629 A1 | 8/2005 |
| WO | WO 2005/096982 | 10/2005 |
| WO | WO 2005/104977 | 11/2005 |
| WO | WO 2005/104978 | 11/2005 |
| WO | WO 2006/044367 A1 | 4/2006 |
| WO | WO 2006/060631 A1 | 6/2006 |
| WO | WO 2006/078236 A1 | 7/2006 |
| WO | WO 2008/021494 | 2/2008 |
| WO | WO 2008/064126 A2 | 5/2008 |
| WO | WO 2008/064346 A2 | 5/2008 |
| WO | WO 2008/130355 A1 | 10/2008 |

OTHER PUBLICATIONS

National Institute of Arthritis and Musculoskeletal and Skin Diseases (NIAMS), "Questions & Answers about . . . Knee Problems", 36 pp. (May 2001).
Smith & Nephew Total Hip Replacement Surgery, HipReplacementInfo.com, 3 pages, Nov. 8, 2005 http://www/hipreplacementinfo.com/hip-total-replacement.htm.
Smith & Nephew Brochure, Design Features, "Opera" pp. 4-15 (1999).
Corinth Surgeon Performs Revolutionary Hip Replacement , Mississippi Medical News, pp. 1-2 (Nov. 17, 2005) http://host1.bondware.com/~mississippi/news.php?viewStory=347.
Dario, et al., 'Smart Surgical Tools and Augmenting Devices,' IEEE Trans. Rob. Autom., 19(5):782-792 (2003).
Fernandez-Lozano, et al., 'Human-machine interface evaluation in a computer assisted surgical system,' Proc. IEEE Int. Conf. Rob. Autom., 2004:231-236 (2004).
Martelli, et al., 'Criteria of interface evaluation for computer assisted surgery systems,' Int. J. Med. Informatics, 72:35-45 (2003).
Visarius, et al., 'Man-machine interfaces in computer assisted surgery.' Computer Aided Surgery, pp. 102-107 (2004).
DePuy, A Johnson & Johnson Company, Brochure entitled 'S-ROM Modular Hip System Minimally Invasive Calcar Miller Surgical Technique,' 12 pages (2004).
Hafez, et al., 'Computer-assisted Total Knee Arthroplasty Using Patient-specific Templating,' *Clinical Orthopaedics and Related Research*, No. 444, pp. 184-192 (2006).
AO Development Institute "MEPUC Motorized Exact Positioning Unit for C-arm," one page (Jul. 7, 2003) http://www.ao-asif.ch/development/adi/examples/mepuc.shtml.
AO Development Institute "MEPUC Motorized Exact Positioning Unit . . . " one page (Mar. 26, 2003) http://www/ao-asif.ch/development/adi/examples/mepuc.shtml.
Barnes, et al., "Unicompartmental Knee Arthroplasty," *Bombay Hospital Journal*, Issue Special, pp. 1-5, www.bhj.org/journal/1996/3803_july/special_486.htm.
Bonecraft Carnegie Mellon Computer-Aided Bone Deformity Correction Brochure, pp. 1-5 (undated).
Bonutti, "Total Joint Replacement Surgery in the 21st Century—New 'Limited-Incision' Total Knee Replacement Offers Important Advantages," 01 page (undated).
Bonutti, et al., "Minimal Incision Total Knee Arthroplasty Using the Suspended Leg Technique," Orthopedics, (published Sep. 2003), 6 pages http://www.orthobluejournal.com/0903/9tips.asp.
BrainLAB Brochure entitled "Ortho . . . Your Partner for the Future" pp. 1-28 (2002).

Croitoru, et al., "Fixation-Based Surgery: A New Technique for Distal Radius Osteotomy," *Clinical Paper, Computer Aided Surgery* 2001, 160-169, vol. 6 (2001).

Delp, et al., "Computer-Assisted Knee Replacement," *Clinical Orthopaedics and Related Research*, 354:49-56 (1998).

Deluzio, et al., "Static alignment and the adduction moment in unicompartmental arthroplasty patients," Presented at NACOB 98: North American Congress on Biomechanics, University of Waterloo, Ontario, Canada, Aug. 14-18, 1998.

DiGioia, et al., "Computer Assisted Orthopedic Surgery," *Clinical Orthopaedics and Related Research*, Sep. 1998, vol. 354, pp. 8-16.

Ellis, et al., "A Surgical Planning and Guidance System for High Tibial Osteotomy," *Journal of Computer-Assisted Surgery*, 4(5):264-274 (1999).

Foley, et al., "Percutaneous pedicle screw fixation of the lumbar spine," *Neurosurg. Focus*, vol. 10(4), pp. 1-8 (2001).

Glossop, http:/www/traxta.com/papers/cua/model.html, 8 pages (Feb. 6, 2002).

ION™ Smith & Nephew Orthopaedics Brochure entitled "You'll Never Look At Your Patients the Same Way Again." 10 pages (Jan. 2001).

Iyun, et al., "Planning and Performing the Ilizarov Method with the Taylor Spatial Frame," Abstract, at $2^{nd}$ Annual Meeting of International Society for Computer Assisted Orthopaedic Surgery, Jun. 21, 2002, pp. 145-147.

Kanade, et al., "Image-Based Computer Assisted Orthopedic Surgery System," Bonecraft, Inc., 12 pages, Apr. 30, 2001.

Kiefer, et al., "Computer Aided Knee Arthroplasty Versus Conventional Technique—First Results," First Annual Meeting of the International Society for Computer Assisted Orthopedic Surgery, Davos, Switzerland, Feb. 8-10, 2001.

Kunz, et al., "Development and Verification of a Non-CT Based Total Knee Arthroplasty System for the LCS Prosthesis," First Annual Meeting of the International Society for Computer Assisted Orthopedic Surgery, Davos, Switzerland, Feb. 8-10, 2001.

Medtronic Surgical Navigation Technologies "Overview Image-Guided Surgery an Advanced Solution to Traditional Surgery," two pages (undated).

Medtronic Surgical Navigation Technologies SNT VERTEK photograph, one page (undated).

Medtronic Surgical Navigation Technologies System Components photograph VERTEK Platform, one page (undated).

Munoz, et al., "Computer Assisted Planning of Hig Tibial Osteotomy for the Treatment of Knee Osteoarthritis," http://www.utc.fr/esb/esb09/abs_htm/570.html (Feb. 21, 2002) (three pages).

Patent Abstracts of Japan, vol. 2002, No. 5, May 3, 2002 & JP 2002 017740A (Ochi Takahiro; Yonenobu Sakuo: MMT:KK) Jan. 22, 2002 Abstract.

Picard, et al., "Kneenav.TKR: Concept and Clinical Application," Computer Assisted Orthopedic Surgery USA 2000 Meeting, Pittsburgh, PA., Jun. 15-17, 2000.

Saragaglia, et al., "Computer Assisted Total Knee Arthroplasty: Comparison with a Conventional Procedure. Results of a 50 Cases Prospective Randomized Study," First Annual Meeting of the International Society for Computer Assisted Orthopedic Surgery, Davos, Switzerland, Feb. 8-10, 2001.

Simon, et al., "The Fundamentals of Virtual Fluoroscopy," Medtronic Surgical Navigation Technologies, Medtronic, pp. 57-66, Computer Assisted Orthopedic Surgery USA 2000 Meeting, Pittsburgh, PA, Jun. 15-17, 2000.

Smith & Nephew—Orthopaedics—CAS—Knees Computer Assisted Total Knee Replacement Surgery, 02 pages (Oct. 13, 2004) http://ortho.smith-nephew.com/us/Standard.asp?NodeId=3396.

Smith & Nephew—Orthopaedics—TriGen Flexible Reamer System http://www.smithnephew.com/US/Standard.asp?NodeID=2998, 02 pages (Jan. 21, 2003).

Smith & Nephew—Orthopaedics—TriGen Reducer http://www.smithnephew.com/US/Standard.asp?NodeID=2996, one page (Jan. 21, 2003).

Smith & Nephew Brochure entitled "Surgical Technique Mini Incision Hip Posterior Approach," 20 pages (Mar. 2003).

Smith & Nephew First Choice in Orthopaedics Brochure Entitled "Achieve Computer Assisted Surgery Trauma Applications the Orbiter Base Station & Satellite Surgical Platform," 18 pages (undated).

Smith & Nephew Genesis II "Total Knee System Primary Surgical Technique," Brochure, pp. 1-36 (Mar. 2001).

Smith & Nephew Richards Genesis® "Total Knee System Primary Surgical Technique Anterior Referencing Instrumentation," pp. 59 (Dec. 1993).

Smith & Nephew Richards Genesis® Total Knee System, "Revision Posterior Referencing Instrumentaion Surgical Technique," Brochure, pp. 1-51 (Dec. 1993).

Stryker Navigation System brochure entitled ". . . best alignment for gap kinematics," 6 pages (2001).

Sugano, et al., "Medical Robotics and Computer-Assisted Surgery in the Surgical Treatment of Patients and Rheumatic Diseases," *Cutting Edge Reports*, http://www/rheuma21st.com/archives/cutting_edge_Robotics_Japan.html (Apr. 27, 2000).

Suhm, et al., "Adapting the C-Arm Fluoroscope for Image Guided Orthopaedic Surgery," CAOS, pp. 212-214 (2002).

Tenbusch, et al., "First Results Using the Robodoc® System for Total Knee Replacement," First Annual Meeting of the International Society for Computer Assisted Orthopedic Surgrey, Davos, Switzerland, Feb. 8-10, 2001.

Tricon Total Knee System, "TRICON-M® with PRO-FIT™ Surgical Procedures," Richards Brochure, pp. 1-29 (undated).

Valstar, et al., "Towards computer-assisted surgery in should joint replacement," *ISPRS Journal of Photogrammetry & Remote Sensing*, 56:326-337 (2002).

\* cited by examiner

COMPUTER-AIDED METHODS, SYSTEMS, AND APPARATUSES FOR SHOULDER ARTHROPLASTY

RELATED APPLICATION

The present application claims priority to U.S. Provisional Ser. No. 60/564,162, entitled "Image Guided Surgery for Shoulder Arthroplasty," filed on Apr. 21, 2004, the contents of which are incorporated herein by reference.

FIELD OF THE INVENTION

The invention relates to computer-aided surgery, and more particularly relates to methods, systems, and apparatuses for providing computer-aided surgical navigation systems for shoulder arthroplasty.

BACKGROUND

Many surgical procedures require a wide array of instrumentation and other surgical items. Such items may include, but are not limited to: sleeves to serve as entry tools, working channels, drill guides and tissue protectors; scalpels; entry awls; guide pins; reamers; reducers; distractors; guide rods; endoscopes; arthroscopes; saws; drills; screwdrivers; awls; taps; osteotomes, wrenches, trial implants and cutting guides. In many surgical procedures, including orthopedic procedures, it may be desirable to associate some or all of these items with a guide and/or handle incorporating a navigational reference, allowing the instrument to be used with a computer-aided surgical navigation system.

Several manufacturers currently produce computer-aided surgical navigation systems. The TREON™ and ION™ systems with FLUORONAV™ software manufactured by Medtronic Surgical Navigation Technologies, Inc. are examples of such systems. The BrainLAB VECTORVISION™ system is another example of such a surgical navigation system. Systems and processes for accomplishing computer-aided surgery are also disclosed in U.S. Ser. No. 10/084,012, filed Feb. 27, 2002 and entitled "Total Knee Arthroplasty Systems and Processes"; U.S. Ser. No. 10/084,278, filed Feb. 27, 2002 and entitled "Surgical Navigation Systems and Processes for Unicompartmental Knee Arthroplasty"; U.S. Ser. No. 10/084,291, filed Feb. 27, 2002 and entitled "Surgical Navigation Systems and Processes for High Tibial Osteotomy"; International Application No. US02/05955, filed Feb. 27, 2002 and entitled "Total Knee Arthroplasty Systems and Processes"; International Application No. US02/05956, filed Feb. 27, 2002 and entitled "Surgical Navigation Systems and Processes for Unicompartmental Knee Arthroplasty"; International Application No. US02/05783 entitled "Surgical Navigation Systems and Processes for High Tibial Osteotomy"; U.S. Ser. No. 10/364,859, filed Feb. 11, 2003 and entitled "Image Guided Fracture Reduction," which claims priority to U.S. Ser. No. 60/355,886, filed Feb. 11, 2002 and entitled "Image Guided Fracture Reduction"; U.S. Ser. No. 60/271,818, filed Feb. 27, 2001 and entitled "Image Guided System for Arthroplasty"; and U.S. Ser. No. 10/229,372, filed Aug. 27, 2002 and entitled "Image Computer Assisted Knee Arthroplasty", the entire contents of each of which are incorporated herein by reference as are all documents incorporated by reference therein.

These systems and processes use position and/or orientation tracking sensors such as infrared sensors acting stereoscopically or other sensors acting in conjunction with navigational references to track positions of body parts, surgery-related items such as implements, instrumentation, trial prosthetics, prosthetic components, and virtual constructs or references such as rotational axes which have been calculated and stored based on designation of bone landmarks. Sensors, such as cameras, detectors, and other similar devices, are typically mounted overhead with respect to body parts and surgery-related items to receive, sense, or otherwise detect positions and/or orientations of the body parts and surgery-related items. Processing capability such as any desired form of computer functionality, whether standalone, networked, or otherwise, takes into account the position and orientation information as to various items in the position sensing field (which may correspond generally or specifically to all or portions or more than all of the surgical field) based on sensed position and orientation of their associated navigational references, or based on stored position and/or orientation information. The processing functionality correlates this position and orientation information for each object with stored information, such as a computerized fluoroscopic imaged file, a wire frame data file for rendering a representation of an instrument component, trial prosthesis or actual prosthesis, or a computer generated file relating to a reference, mechanical, rotational or other axis or other virtual construct or reference. The processing functionality then displays position and orientation of these objects on a rendering functionality, such as a screen, monitor, or otherwise, in combination with image information or navigational information such as a reference, mechanical, rotational or other axis or other virtual construct or reference. Thus, these systems or processes, by sensing the position of navigational references, can display or otherwise output useful data relating to predicted or actual position and orientation of surgical instruments, body parts, surgically related items, implants, and virtual constructs for use in navigation, assessment, and otherwise performing surgery or other operations.

Some of the navigational references used in these systems may emit or reflect infrared light that is then detected by an infrared camera. The references may be sensed actively or passively by infrared, visual, sound, magnetic, electromagnetic, x-ray or any other desired technique. An active reference emits energy, and a passive reference merely reflects energy. Some navigational references may have markers or fiducials that are traced by an infrared sensor to determine the position and orientation of the reference and thus the position and orientation of the associated instrument, item, implant component or other object to which the reference is attached.

In addition to navigational references with fixed fiducials, modular fiducials, which may be positioned independent of each other, may be used to reference points in the coordinate system. Modular fiducials may include reflective elements which may be tracked by two, sometimes more, sensors whose output may be processed in concert by associated processing functionality to geometrically calculate the position and orientation of the item to which the modular fiducial is attached. Like fixed fiducial navigational references, modular fiducials and the sensors need not be confined to the infrared spectrum—any electromagnetic, electrostatic, light, sound, radio frequency or other desired technique may be used. Similarly, modular fiducials may "actively" transmit reference information to a tracking system, as opposed to "passively" reflecting infrared or other forms of energy.

Navigational references useable with the above-identified navigation systems may be secured to any desired structure, including the above-mentioned surgical instruments and other items. The navigational references may be secured directly to the instrument or item to be referenced. However, in many instances it will not be practical or desirable to secure the navigational references to the instrument or other item. Rather, in many circumstances it will be preferred to secure the navigational references to a handle and/or a guide adapted to receive the instrument or other item. For example, drill bits and other rotating instruments cannot be tracked by securing the navigational reference directly to the rotating instrument because the reference would rotate along with the instrument. Rather, a preferred method for tracking a rotating instrument is to associate the navigational reference with the instrument or item's guide or handle.

Computer-aided surgical navigation systems have been developed for various surgeries, but currently none exists for shoulder arthroplasty or hemiarthroplasty that includes features according to the present invention.

One of the leading causes for revision after shoulder arthroplasty is misalignment of the implant. Currently, instrumentation design limits alignment of the humeral resection to average values for inclination and version. While some instrumentation designs allow for adjustability of inclination and offset, assessment is still made qualitatively. Also, surgeons often use visual landmarks, or "rules of thumb," which can be misleading due to anatomical variability.

Another problem arising in shoulder arthroplasty is that surgeons cannot resurface the glenoid due to a lack of exposure. Exposure in shoulder arthroplasty is limited due to the extensive amount of soft tissue surrounding the shoulder compartment. Because of this problem, surgeons may be able to perform only a hemiarthroplasty in which only the humeral head is replaced.

Yet another problem unique to shoulder arthroplasty is the difficulty in determining the thickness of the scapula. Such a determination is necessary to prevent breakthrough during preparation of the glenoid.

In fracture situations, it is difficult to determine the inferior/superior position of the humeral head due to the absence of landmarks. Malpositioning of the humeral head can lead to instability of the shoulder and even dislocation.

The surgeon also relies on instrumentation to predict the appropriate size for the humerus and the glenoid instead of the ability to intraoperatively template the appropriate size of the implants for optimal performance.

Another challenge for surgeons is soft tissue balancing after the implants have been positioned. Releasing some of the soft tissue attachment points can change the balance of the shoulder; however, the multiple options can be confusing for many surgeons. In revision shoulder arthroplasty, many of the visual landmarks are no longer present, making alignment and restoration of the joint line difficult.

Thus, what is needed are systems and processes that allow a surgeon to use patient-specific measurements to determine proper alignment of implants and appropriate revision in shoulder arthroplasty.

Also needed are systems and processes that assist in the appropriate placement of shoulder arthroplasty components and in the evaluation of that placement. Systems and methods for performing soft tissue balancing in shoulder arthroplasty are also needed.

Also needed are systems and methods that address some or all of the problems mentioned above.

SUMMARY

Some embodiments of the invention include a method for performing shoulder arthroplasty or hemiarthroplasty surgical operations on portions of a shoulder joint. The method includes:

(a) attaching at least one first navigational reference capable of being tracked by a navigational sensor to a body part forming at least a portion of the shoulder joint,
(b) generating navigational reference information relating to position and orientation of the body part,
(c) storing at least some of the navigational reference information in a computer,
(d) attaching at least one second navigational reference capable of being tracked by a navigational sensor to a surgical instrument,
(e) receiving information from the navigational sensor regarding the position and orientation of the surgical instrument with respect to the body part, and
(f) navigating the surgical instrument relative to the body part according to the position and orientation information.

Other embodiments of the invention include a method for performing shoulder arthroplasty or hemiarthroplasty surgical operations on portions of a shoulder joint. The method includes:

(a) attaching at least one first navigational reference capable of being tracked by a navigational sensor to a body part forming at least a portion of the shoulder joint,
(b) generating navigational reference information relating to position and orientation of the body part,
(c) storing at least some of the navigational reference information in a computer,
(d) attaching at least one second navigational reference capable of being tracked by a navigational sensor to a surgical instrument,
(e) receiving information from the second navigational sensor regarding the position and orientation of the surgical instrument with respect to the body part,
(f) navigating the surgical instrument relative to the body part according to the position and orientation information,
(g) modifying the body part using the surgical instrument,
(h) generating and displaying on a monitor associated with the computer information regarding the modification of the body part,
(i) tracking a trial component using at least one of the navigational sensors,
(j) receiving information from at least one of the navigational sensor regarding the position and orientation of the trial component with respect to the body part,
(k) generating and displaying on the monitor associated with the computer a visual image of the trial component properly positioned and oriented relative to the body part, and
(l) navigating the trial component relative to the body part and attaching the trial component to the body part according to the image.

Some embodiments of the invention include a method for performing shoulder arthroplasty or hemiarthroplasty surgical operations on portions of a shoulder joint. The method includes:

(a) attaching at least one first navigational reference capable of being tracked by a navigational sensor to a body part forming at least a portion of the shoulder joint,
(b) generating navigational reference information relating to position and orientation of a body part forming at least a portion of the shoulder joint,
(c) storing at least some of the navigational reference information in a computer,
(d) attaching at least one second navigational reference capable of being tracked by a navigational sensor to a surgical instrument, (e) receiving information from the second navigational sensor regarding the position and orientation of the surgical instrument with respect to the body part,
(f) navigating the surgical instrument relative to the body part according to the position and orientation information,
(g) modifying the body part using the surgical instrument,
(h) generating and displaying on a monitor associated with the computer information regarding the modification of the body part,
(i) tracking a prosthetic component using at least one of the navigational sensors,
(j) receiving information from at least one of the navigational sensor regarding the position and orientation of the prosthetic component with respect to the body part,
(k) generating and displaying on the monitor associated with the computer a visual image of the prosthetic component properly positioned and oriented relative to the body part, and
(l) navigating the prosthetic component relative to the body part and attaching the prosthetic component to the body part according to the image.

Some embodiments of the invention include a method for performing shoulder arthroplasty or hemiarthroplasty surgical operations on portions of a shoulder joint. The method includes:
(a) attaching at least one first navigational reference capable of being tracked by a navigational sensor to a humerus forming at least a portion of the shoulder joint,
(b) generating navigational reference information relating to position and orientation of the humerus,
(c) storing at least some of the navigational reference information in a computer,
(d) attaching at least one second navigational reference capable of being tracked by a navigational sensor to a humeral reamer,
(e) receiving information from the navigational sensor regarding the position and orientation of the humeral reamer with respect to the humerus, and
(f) navigating the humeral reamer relative to the humerus according to the position and orientation information.

Other embodiments of the invention include a method for performing shoulder arthroplasty or hemiarthroplasty surgical operations on portions of a shoulder joint; the method includes:
(a) attaching at least one first navigational reference capable of being tracked by a navigational sensor to a glenoid fossa forming at least a portion of the shoulder joint,
(b) generating navigational reference information relating to position and orientation of the glenoid fossa,
(c) storing at least some of the navigational reference information in a computer,
(d) attaching at least one second navigational reference capable of being tracked by a navigational sensor to a glenoid reamer,
(e) receiving information from the navigational sensor regarding the position and orientation of the glenoid reamer with respect to the glenoid fossa, and
(f) navigating the glenoid reamer relative to the glenoid fossa according to the position and orientation information.

Some embodiments of the invention include a method for performing shoulder arthroplasty or hemiarthroplasty surgical operations on portions of a shoulder joint. The method includes:
(a) attaching at least one first navigational reference capable of being tracked by a navigational sensor to a humerus forming at least a portion of the shoulder joint,
(b) generating navigational reference information relating to position and orientation of the humerus,
(c) storing at least some of the navigational reference information in a computer,
(d) attaching at least one second navigational reference capable of being tracked by a navigational sensor to a humeral reamer,
(e) receiving information from the navigational sensor regarding the position and orientation of the humeral reamer with respect to the humerus,
(f) navigating the humeral reamer relative to the humerus according to the position and orientation information, and
(g) attaching a cutting block to the humeral reamer.

Some embodiments of the invention include a method for performing shoulder arthroplasty or hemiarthroplasty surgical operations on portions of a shoulder joint. The method includes:
(a) attaching at least one first navigational reference capable of being tracked by a navigational sensor to a humerus forming at least a portion of the shoulder joint,
(b) generating navigational reference information relating to position and orientation of the humerus,
(c) storing at least some of the navigational reference information in a computer,
(d) attaching at least one second navigational reference capable of being tracked by the navigational sensor to a humeral reamer,
(e) receiving information from the navigational sensor regarding the position and orientation of the humeral reamer with respect to the humerus,
(f) navigating the humeral reamer relative to the humerus according to the position and orientation information,
(g) attaching a cutting block to the humeral reamer,
(h) attaching at least one third navigational reference capable of being tracked by the navigational sensor to the cutting block, and
(i) positioning the cutting block in at least one rotational degree of freedom through a range motion with infinite positions in the range; and at least one translational degree of freedom through a range of motion with infinite positions in the range,
(j) receiving continuous information from the navigational sensor regarding the position and orientation of the cutting block with respect to the humerus or the humeral reamer, wherein the information comprises rotational information in at least one degree of freedom and translational information in at least one degree of freedom.

Some embodiments of the invention include a computer-aided surgical navigation system for performing shoulder arthroplasty or hemiarthroplasty. The system includes:
(a) a sensor adapted receive information regarding position and orientation of at least one reference;
(b) a reference adapted to be mounted to a body part forming at least a portion of the shoulder joint;
(c) a reference adapted to be mounted to a surgical instrument for use in performing shoulder arthroplasty or hemiarthroplasty;
(d) a processor adapted to receive and store information from the sensor in order to track a position and orientation of the at least one surgical reference with respect to the body part; and (e) a monitor adapted to receive information from the processor in order to display at least some of the navigational reference information and the at least one surgical reference.

In some embodiments of the invention, the body part is the humerus. In other embodiments, the body part is the glenoid.

In some embodiments, the surgical instrument is a reamer, a resection guide, a cutting block or a probe. In some more particular embodiments, the surgical instrument is a humeral reamer or a glenoid reamer.

DETAILED DESCRIPTION

This invention will now be described more fully with reference to the drawings, showing preferred embodiments of the invention. However, this invention can be embodied in many different forms and should not be construed as limited to the embodiments set forth.

Systems and processes according to some embodiments of the invention use computing capacity, including stand-alone and/or networked, to determine and/or store data regarding spatial aspects of surgically related items and virtual constructs or references, including body parts, implements, instrumentation, trial components, prosthetic components and anatomical, mechanical and rotational axes of body parts. Any or all of these may be physically or virtually connected to or incorporate any desired form of mark, structure, component, or other fiducial or reference device or technique which allows position and/or orientation of the item to which it is attached to be sensed and tracked, preferably in three dimensions of translations and varying degrees of rotation as well as in time, if desired.

Systems and processes according to some embodiments of the invention employ computing means to calculate and store references axes of body components such as in shoulder arthroplasty, for example the anatomical axis of the humerus and the retroversion reference axis. From these axes such systems track the position of the instrumentation and osteotomy guides so that bone resections will locate the implant position optimally, usually aligned with the anatomical axis. Furthermore, during trial reduction of the shoulder, the systems provide feedback on the balancing of the soft tissue in a range of motion and under stresses and can suggest or at least provide more accurate information than in the past about which ligaments the surgeon should release in order to obtain correct balancing, alignment and stability. Systems and processes according to some embodiments of the present invention can also suggest modifications to implant size, positioning, and other techniques to achieve optimal kinematics. They can also include databases of information regarding tasks such as ligament balancing, in order to provide suggestions to the surgeon based on performance of test results as automatically calculated by such systems and processes.

Figure 1:
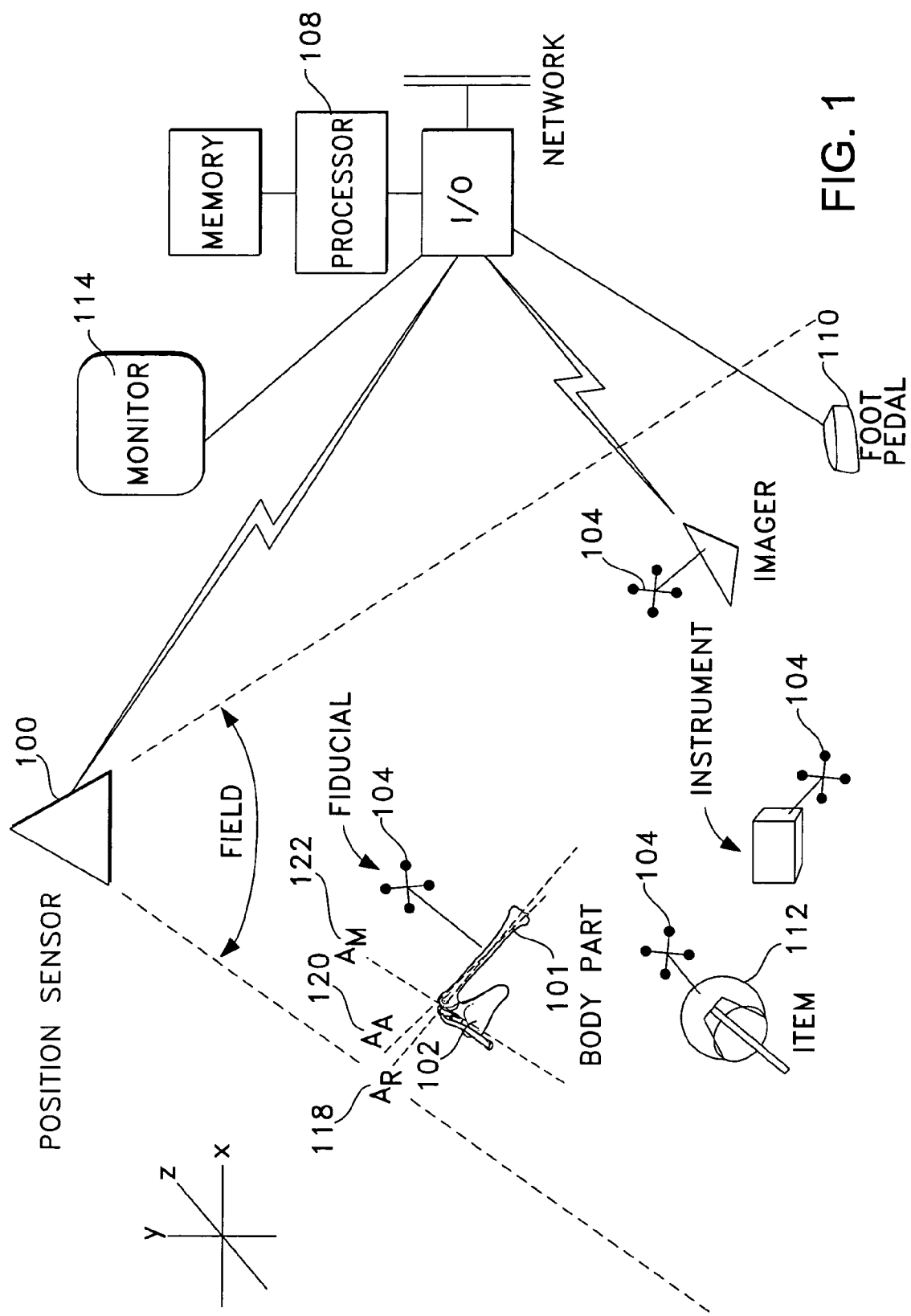
FIG. 1 is schematic view showing an environment for using a computer-aided surgical navigation system according to some embodiments of the invention in a shoulder arthroplasty or semiarthroplasty.

FIG. 1 is a schematic view showing an environment for using a computer-aided surgical navigation system according to some embodiments of the present invention in a surgery on a shoulder, in this case a shoulder arthroplasty. Systems and processes according to some embodiments of the invention can track various body parts such as humerus 101 and scalpula 102 to which navigational sensors 100 may be implanted, attached or associated physically, virtually or otherwise.

Navigational sensors 100 may be used to determine and track the position of body parts, axes of body parts, implements, instrumentation, trial components and prosthetic components. Navigational sensors 100 may use infrared, electromagnetic, electrostatic, light sound, radio frequency or other desired techniques.

The navigational sensor 100 may be used to sense the position and orientation of navigational references 104 and therefore items with which they are associated. A navigational reference 104 can include fiducial markers, such as marker elements, capable of being sensed by a navigational sensor in a computer-aided surgical navigation system. The navigational sensor 100 may sense active or passive signals from the navigational references 104. The signals may be electrical, magnetic, electromagnetic, sound, physical, radio frequency, optical or visual, or other active or passive technique. For example in one embodiment, the navigational sensor 100 can visually detect the presence of a passive-type navigational reference. In an example of another embodiment, the navigational sensor 100 can receive an active signal provided by an active-type navigational reference. The surgical navigation system can store, process and/or output data relating to position and orientation of navigational references 104 and thus, items or body parts, such as 101 and 102 to which they are attached or associated.

In the embodiment shown in FIG. 1, computing functionality 108 such as one or more computer programs can include processing functionality, memory functionality, input/output functionality whether on a standalone or distributed basis, via any desired standard, architecture, interface and/or network topology. In one embodiment, computing functionality 108 can be connected to a monitor 114 on which graphics and data may be presented to a surgeon during surgery. The monitor 114 preferably has a tactile interface so that the surgeon may point and click on monitor 114 for tactile screen input in addition to or instead of, if desired, keyboard and mouse conventional interfaces. Additionally, a foot pedal 110 or other convenient interface may be coupled to computing functionality 108 as can any other wireless or wireline interface to allow the surgeon, nurse or other user to control or direct functionality 108 in order to, among other things, capture position/orientation information when certain components are oriented or aligned properly. Items 112 such as trial components, instrumentation components may be tracked in position and orientation relative to body parts 101 and 102 using one or more navigational references 104.

Computing functionality 108 can, but need not, process, store and output on monitor 114 various forms of data that correspond in whole or part to body parts 101 and 202 and other components for item 112. For example, body parts 101 and 102 can be shown in cross-section or at least various internal aspects of them such as bone canals and surface structure can be shown using fluoroscopic images. These images can be obtained using an imager 113, such as a C-arm attached to a navigational reference 104. The body parts, for example, humerus 101 and scapula 102, can also have navigational references 104 attached. When fluoroscopy images are obtained using the C-arm with a navigational reference 104, a navigational sensor 100 "sees" and tracks the position of the fluoroscopy head as well as the positions and orientations of the humerus 101 and scapula 102. The computer stores the fluoroscopic images with this position/orientation information, thus correlating position and orientation of the fluoroscopic image relative to the relevant body part or parts. Thus, when the humerus 101 and corresponding navigational reference 104 move, the computer automatically and correspondingly senses the new position of humerus 101 in space and can correspondingly move implements, instruments, references, trials and/or implants on the monitor 114 relative to the image of humerus 101. Similarly, the image of the body part can be moved, both the body part and such items may be moved, or the on-screen image otherwise presented to suit the preferences of the surgeon or others and carry out the imaging that is desired. Similarly, when an item 112, such as a stylus, cutting block, reamer, drill, saw, extramedullary rod, intramedullar rod, or any other type of item or instrument, that is being tracked moves, its image moves on monitor 114 so that the monitor 114 shows the item 112 in proper position and orientation on monitor 114 relative to the humerus 101. The item 112 can thus appear on the monitor 114 in proper or improper alignment with respect to the mechanical axis and other features of the humerus 101, as if the surgeon were able to see into the body in order to navigate and position item 112 properly.

The computing functionality 108 can also store data relating to configuration, size and other properties of items 112 such as joint replacement prostheses, implements, instrumentation, trial components, implant components and other items used in surgery. When those are introduced into the field of position/orientation sensor 100, computing functionality 108 can generate and display overlain or in combination with the fluoroscopic images of the body parts 101 and 102, computer generated images of joint replacement prostheses, implements, instrumentation components, trial components, implant components and other items 112 for navigation, positioning, assessment and other uses.

Instead of or in combination with fluoroscopic, MRI or other actual images of body parts, computing functionality 108 may store and output navigational or virtual construct data based on the sensed position and orientation of items in the surgical field, such as surgical instruments or position and orientation of body parts. For example, monitor 114 can output a resection plane, anatomical axis, mechanical axis, anterior/posterior reference plane, medial/lateral reference plane, rotational axis or any other navigational reference or information that may be useful or desired to conduct surgery. In the case of the reference plane, for example, monitor 114 can output a resection plane that corresponds to the resection plane defined by a cutting guide whose position and orientation is being tracked by navigational sensors 100. In other embodiments, monitor 114 can output a cutting track based on the sensed position and orientation of a reamer. Other virtual constructs can also be output on monitor 114, and can be displayed with or without the relevant surgical instrument, based on the sensed position and orientation of any surgical instrument or other item in the surgical field to assist the surgeon or other user to plan some or all of the stages of the surgical procedure.

In some embodiments of the present invention, computing functionality 108 can output on monitor 114 the projected position and orientation of an implant component or components based on the sensed position and orientation of one or more surgical instruments associated with one or more navigational references 104. For example, the system may track the position and orientation of a cutting block as it is navigated with respect to a portion of a body part that will be resected. Computing functionality 108 may calculate and output on monitor 114 the projected placement of the implant in the body part based on the sensed position and orientation of the cutting block, in combination with, for example, the mechanical axis of the humerus and/or the shoulder, together with axes showing the anterior/posterior and medial/lateral planes. No fluoroscopic, MRI or other actual image of the body part is displayed in some embodiments, since some hold that such imaging is unnecessary and counterproductive in the context of computer aided surgery if relevant axis and/or other navigational information is displayed. Additionally, some systems use "morphed" images that change shape to fit data points or they use generic graphics or line art images with the data points displayed in a relatively accurate position or not displayed at all. If the surgeon or other user is dissatisfied with the projected placement of the implant, the surgeon may then reposition the cutting block to evaluate the effect on projected implant position and orientation.

Additionally, computer functionality 108 can track any point in the navigational sensor 100 field such as by using a designator or a probe 116. The probe also can contain or be attached to a navigational reference 104. The surgeon, nurse, or other user touches the tip of probe 116 to a point such as a landmark on bone structure and actuates the foot pedal 110 or otherwise instructs the computer 108 to note the landmark position. The navigational sensor 100 "sees" the position and orientation of navigational reference 104 "knows" where the tip of probe 116 is relative to that navigational reference 104 and thus calculates and stores, and can display on monitor 114 whenever desired and in whatever form or fashion or color, the point or other position designated by probe 116 when the foot pedal 110 is hit or other command is given. Thus, probe 116 can be used to designate landmarks on bone structure in order to allow the computer 108 to store and track, relative to movement of the navigational reference 104, virtual or logical information such as retroversion axis 118, anatomical axis 120 and mechanical axis 122 of scapula 102, humerus 101 and other body parts in addition to any other virtual or actual construct or reference.

Systems and processes according to some embodiments of the present invention can communicate with suitable computer-aided surgical systems and processes such as the BrainLAB VectorVision system, the OrthoSoft Navitrack System, the Stryker Navigation system, the FluoroNav system provided by Medtronic Surgical Navigation Technologies, Inc. and software provided by Medtronic Sofamor Danek Technologies. Such systems or aspects of them are disclosed in U.S. Pat. Nos. 5,383,454; 5,871,445; 6,146,390; 6,165,81; 6,235,038 and 6,236,875; and related (under 35 U.S.C. Section 119 and/or 120) patents, which are all incorporated herein by this reference. Any other desired systems and processes can be used as mentioned above for imaging, storage of data, tracking of body parts and items and for other purposes.

These systems may require the use of reference frame type fiducials which have four, and in some cases five elements, tracked by sensors for position/orientation of the fiducials and thus of the body part, implement, instrumentation, trial component, implant component, or other device or structure being tracked. Such systems can also use at least one probe which the surgeon can use to select, designate, register, or otherwise make known to the system a point or points on the anatomy or other locations by placing the probe as appropriate and signaling or commanding the computer to note the location of, for instance, the tip of the probe. These systems also may, but are not required to, track position and orientation of a C-arm used to obtain fluoroscopic images of body parts to which fiducials have been attached for capturing and storage of fluoroscopic images keyed to position/orientation information as tracked by the sensors. Thus, the monitor can render fluoroscopic images of bones in combination with computer generated images of virtual constructs and references together with implements, instrumentation components, trial components, implant components and other items used in connection with surgery for navigation, resection of bone, assessment and other purposes.

Figure 2:
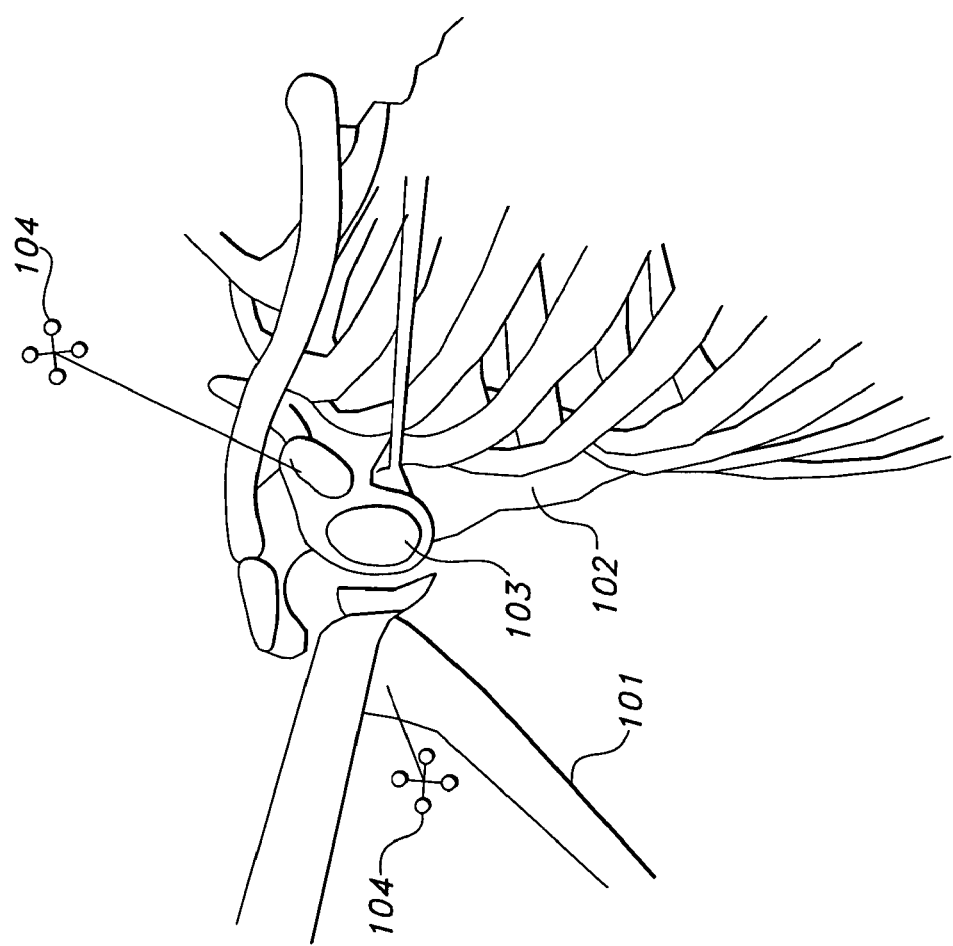
FIG. 2 is view of the shoulder, including a humerus and a scapula to which navigational references according to some embodiments of the invention have been attached.

FIGS. 2-7 are various views associated with shoulder arthroplasty surgery processes according to one embodiment of the invention. FIG. 2 shows a human shoulder, as well as the corresponding the corresponding humerus 101 and scapula 102, to which navigational references 104 have been rigidly attached in accordance with this embodiment of the invention. Attachment of navigational references 104 preferably is accomplished using structure that withstands vibration of surgical saws and other phenomenon which occur during surgery without allowing any substantial movement of navigational references 104 relative to the body part being tracked by the system.

Systems and processes according to various embodiments of the invention can be used with cloud of points-type, registration-type, and other surgical location and preparation techniques and methods. For example, in one prosthetic installation procedure, a surgeon can designate a center of rotation of a patient's humeral head for purposes of establishing the mechanical axis and other relevant constructs relating to the patient's humerus according to which prosthetic components can ultimately be positioned. Such center of rotation can be established by articulating the humerus 101 within the glenoid 103 or a prosthesis to capture a number of samples of position and orientation information and thus in turn to allow the computer to calculate the average center of rotation. The center of rotation can be established by using a probe 116 associated with a navigational reference 104, and designating a number of points on the humeral head and thus allowing the computing functionality 108 to calculate the geometrical center or a center that corresponds to the geometry of points collected. Additionally, graphical representations such as controllably sized circles displayed on the monitor can be fitted by the surgeon to the shape of the humeral head on planar images using tactile input on monitor 114 to designate the centers according to that graphic, such as are represented by the computing functionality 108 as intersection of axes of the circles. Other techniques for determining, calculating or establishing points or constructs in space, whether or not corresponding to bone structure, can be used in accordance with the invention.

In another example, a navigational sensor 100 can be used in designation or registration of items that will be used in surgery. Registration simply means ensuring that the computing functionality 108 knows which body part, item or construct corresponds to which navigational reference or references 104, and how the position and orientation of the body part, item or construct is related to the position and orientation of its corresponding navigational reference or references 104 attached to an impactor or other component which is in turn attached to an item. Such registration or designation can be done before or after registering bone or body parts. In one instance, a technician can designate with a probe 116 an item such as an instrument or component 112 to which a navigational 104 reference is attached. A navigational sensor associated with a computer-aided surgical navigational system can "see" the 100 position and orientation of the navigational reference 104 attached to the item and also the position and orientation of the navigational reference 104 attached to the probe 116 whose tip is touching a landmark on the item 112. The technician can designate onscreen or otherwise the identification of the item 112 and then activates the foot pedal 110 or otherwise instructs the computing functionality 108 to correlate the data corresponding to such identification, such as data needed to represent a particular cutting block component for a particular shoulder implant product, with the navigational reference 104 attached to the component. The computer has then stored identification, position and orientation information relating to the navigational reference 104 for the component correlated with the data such as configuration and shape data for the item 112 so that upon registration, when the navigational sensor 100 can track the item 112 and navigational reference 104 in the infrared field, the monitor 114 can show the cutting block component moving and turning, and properly positioned and oriented relative to the body part or navigational information such as axes which are also being tracked.

Similarly, the mechanical axis and other axes or constructs of body parts can also be "registered" for tracking by the system. Again, the computer-aided surgical navigational system can employ a fluoroscope to obtain images of the patient's humerus and scapula, including the coracoid process, acromion and glenoid, or other body parts, and/or it can allow generation of navigational information regarding such parts, such as for example, generation of anatomical axis 120 information which can be displayed with the position and orientation of devices, components and other structures connected to navigational references 104. In the case of obtaining images, the system can correlate such fluoroscopic images with the position and orientation of the C-arm and the patient anatomy in real time as discussed above with the use of one or more navigational references placed on the body parts before image acquisition and which remain in position during the surgical procedure. Using these axes and constructs and/or images and/or the probe, the surgeon can select and register in the computing functionality 108 the center of the humeral head and elbow in orthogonal views, usually anterior/posterior and lateral, on a touch screen. The surgeon can use the probe 116 to select any desired anatomical landmarks or references at the operative site of the shoulder or on the skin or surgical draping over the skin, as on the elbow. These points can be registered in three-dimensional space by the system and can be tracked relative to the navigational references 104 on the patient anatomy which are preferably placed intraoperatively. Although registering points using actual bone structure is one preferred way to establish the axis, a cloud of points approach by which the probe is used to designate multiple points on the surface of the bone structure can be employed, as can moving the body part and tracking movement to establish a center of rotation as discussed above. Once the center of rotation for the humeral head and the epicondylar axis have been registered, the computer can calculate, store, and render, and otherwise use data for, the mechanical axis of the humerus.

Any desired axes or other constructs can be created, tracked and displayed, in order to model and generate images and data showing any desired static or kinematic function of the shoulder for any purposes related to shoulder arthroplasty.

Figure 4:
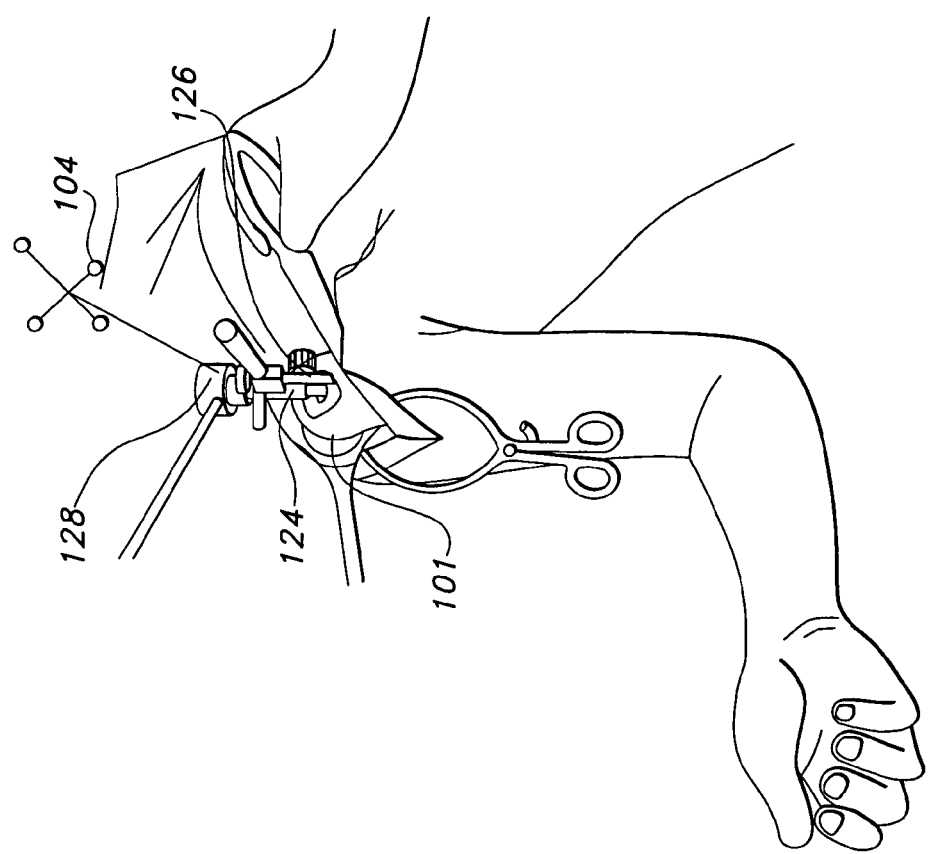
FIG. 4 shows navigation and placement of a resection guide and a cutting block according to some embodiments of the present invention.
Figure 6:
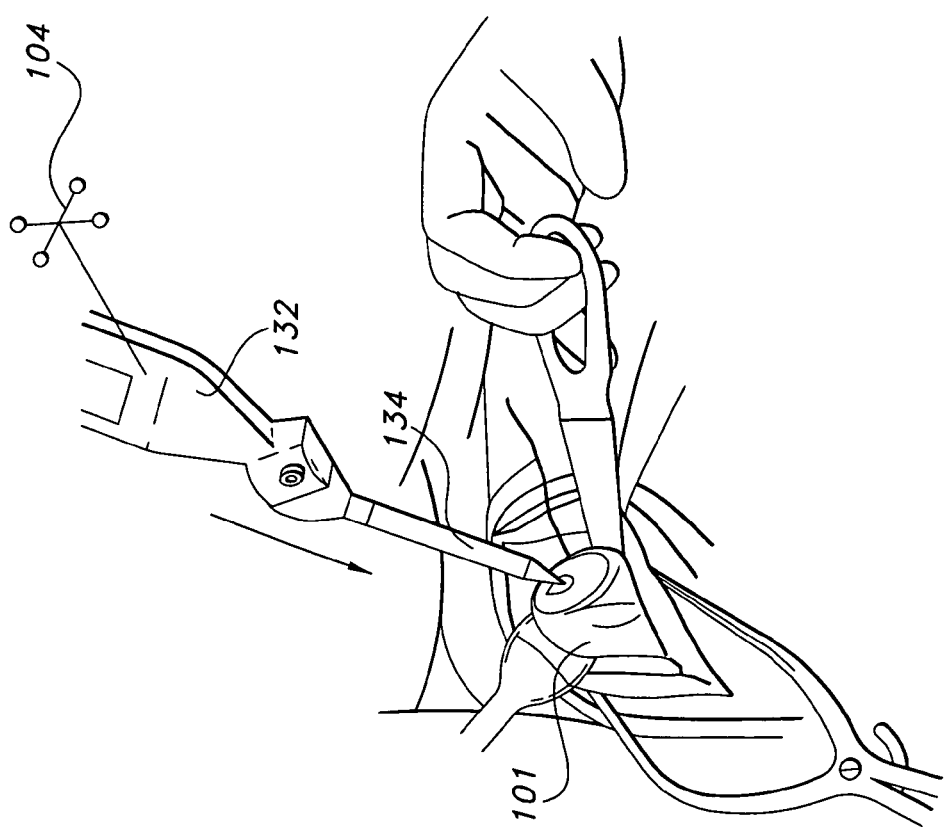
FIG. 6 shows navigation and placement of a humeral trial component on a humerus according to some embodiments of the invention.
Figure 7:
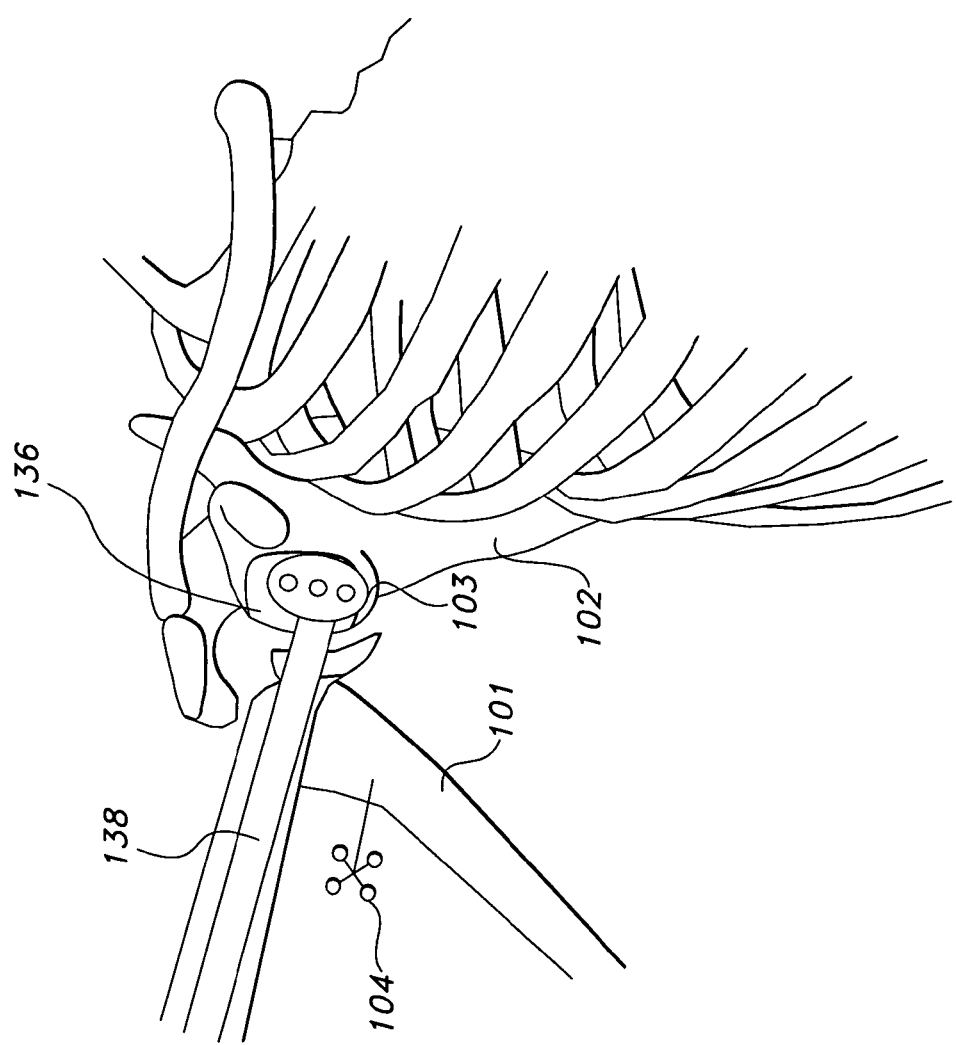
FIG. 7 shows navigation and placement of a drill guide on the glenoid surface according to some embodiments of the invention.

After the mechanical axis and other rotation axes and constructs relating to the humerus and scapula are established, instrumentation can be properly oriented to resect or modify bone in order to fit trial components and implant components properly according to the embodiments shown in FIGS. 6-7. Instrumentation such as, for instance, cutting blocks, to which navigational references 104 are mounted, can be employed as shown in FIG. 4. The system can then track instrumentation as the surgeon manipulates it for optimum positioning. In other words, the surgeon can "navigate" the instrumentation for optimum positioning using the system and the monitor. In this manner, instrumentation may be positioned according to the system of this embodiment in order to align the osteotomies to the mechanical and rotational axes or reference axes on an extramedullary rod that does not violate the canal, on an intramedullary rod, or on any other type of rod. The monitor 114 can then also display the instrument such as the cutting block and/or the implant relative to the instrument and the rod during this process, in order, among other things, to select the proper size of implant and perhaps implant type. As the instrument moves, the flexion/extension and internal/external rotation of the relative component position can be calculated and shown with respect to the referenced axes; in the preferred embodiment, this can be done at a rate of six cycles per second or faster. The instrument position is then fixed in the computing functionality 108 and physically and the bone resections are made.

Systems and processes according to embodiments of the invention can be used to track a humeral reamer to create a virtual anatomical axis of the humerus. The anatomical axis can be stored and subsequently used by the computer.

Figure 3:
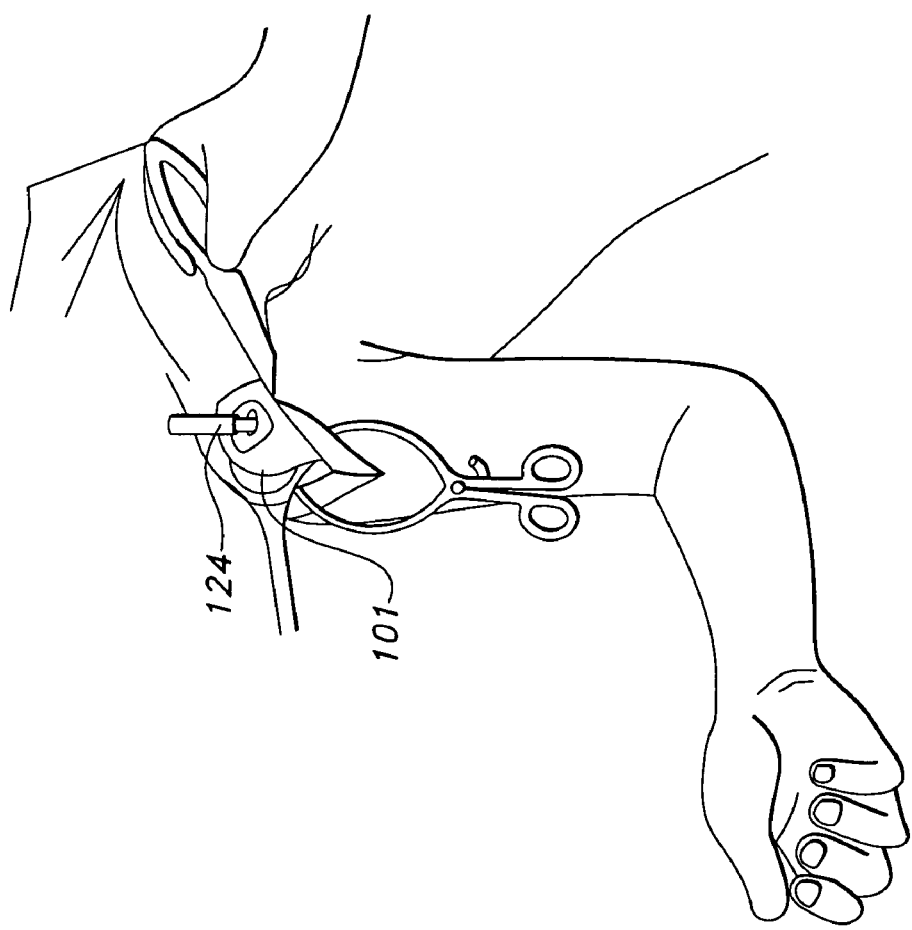
FIG. 3 shows navigation and placement of a humeral reamer according to some embodiments of the present invention.

FIG. 3 shows orientation of an humeral reamer 124 to which a navigational reference 104 is attached. The surgeon views the monitor 114 which has an image of the humeral reamer 124 overlain on or in combination with the humerus 101 fluroroscopic image as the two are actually positioned and oriented relative to one another in space.

Computer-aided surgical navigation systems according to embodiments of the invention may also be used to determine the degree of humeral head retroversion, if any. The retroversion reference axis may be determined by determining the orientation of the proximal articular surface or the humerus with respect to the epicondylar axis of the elbow. This information may be used to control rotation.

Once the humeral reamer 124 has been placed, instrumentation can be positioned as tracked in position and orientation by navigational sensor 100 and displayed on monitor 114. Thus, as shown in FIG. 4, a resection guide 128 and a cutting block 126 of the sort used to establish the humeral anterior cut, with its navigational reference 104 attached, is introduced into the field and positioned on the reamer. Because the cutting block 126 corresponds to a particular implant product and can be adjusted and designated on screen to correspond to a particular implant size of that product, the computing functionality 108 can generate and the monitor 114 can display a graphic of the cutting block 126 and a humeral component overlain on the fluoroscopic image. The surgeon can thus navigate and position the cutting block 126 on monitor 114 using not only images of the cutting block 126 on the bone, but also images of a corresponding humeral component which will be ultimately installed. The surgeon can thus adjust the positioning of the physical cutting block 126, and secure it to the reamer 124 in order to resect the anterior of the humerus 101 in order to optimally fit and position the ultimate humeral component being shown on the monitor 114. Other cutting blocks and other resections may be positioned and made similarly on the humerus 101.

In some embodiments of the invention, the cutting block 126 may be navigated as it moves in six degrees of freedom: three translational and three rotational. For each rotational degree of freedom, the cutting block 126 may be tracked as it moves through a range motion with infinite positions in the range. Likewise, for each translational degree of freedom, the cutting block 126 may be tracked as it moves through a range of motion with infinite positions in the range. In some embodiments, the system receives continuous information from the navigational sensor 100 regarding the position and orientation of the cutting block 126 with respect to the humerus 101 or the humeral reamer 124, wherein the information comprises rotational information in at least one degree of freedom and translational information in at least one degree of freedom. The information may be displayed on the monitor 114, allowing the surgeon immediate and detailed information for positioning the cutting block 126.

In a similar fashion, instrumentation may be navigated and positioned on the glenoid fossa 103 of the scapula 102 and as tracked by navigational sensor 100 and on monitor 114 by images of the cutting block and the implant component.

Figure 5:
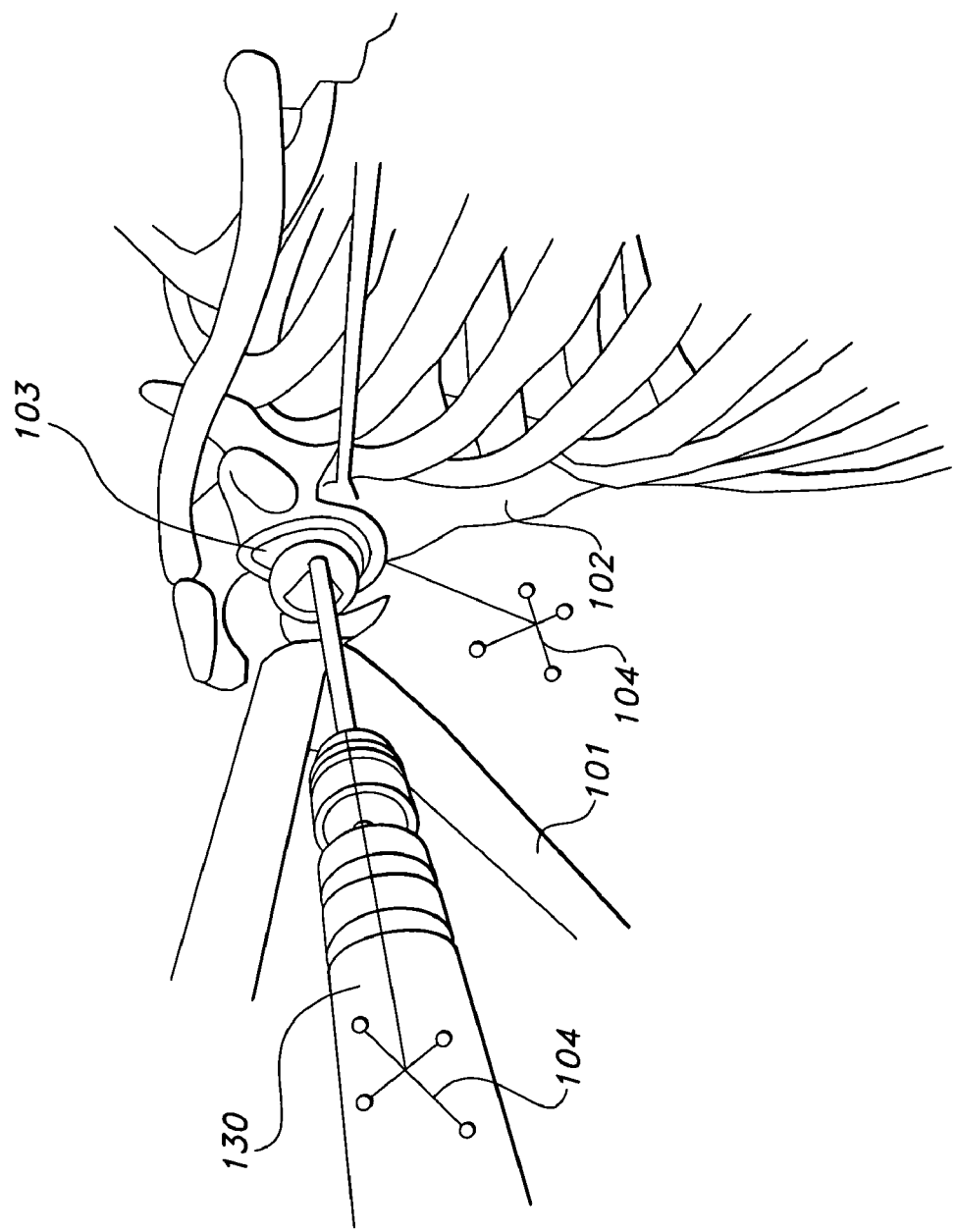
FIG. 5. shows the navigation and reaming the glenoid surface in preparation for a prosthetic glenoid component according to some embodiments of the invention.

As shown in FIG. 5 in a total shoulder arthroplasty, a glenoid reamer may be navigated to determine the depth, position and angle of reaming. Subsequently, navigated glenoid instruments are then used to prepare the glenoid to receive a glenoid component trial. Any appropriate glenoid component or component trial may be used, for example, an all-polyethylene glenoid component with three pegs or one keel or with a metal back. Such glenoid components generally have three screw holes on the glenoid base. Depending on the type of glenoid component used, a drill guide 138 or a keel reamer guide may be used to prepare the glenoid for the glenoid component. A navigated drill guide 138 is shown in FIG. 7.

Once resection and modification of bone has been accomplished, implant trials can then be installed and tracked by the system in a manner similar to navigating and positioning the instrumentation, as displayed on the monitor 114. Thus, a humeral component trial and a glenoid component trial may be placed as navigated on monitor 114 using computing functionality 118 generated overlays corresponding to the trials.

During the trial installation process, and also during the implant component installation process, instrument positioning process or at any other desired point in surgical or other operations according to the invention, the system can transition or segue from tracking a component according to a first navigational reference to tracking the component according to a second navigational reference. Thus, as shown in FIG. 6, the trial humeral component 134 is mounted on an impactor 132 to which is attached a first navigational reference 104. The trial component 134 is installed and positioned using the impactor 132. The computing functionality 108 tracks the position and orientation of the trial component 134 relative to the navigational reference 104 on the impactor 132 (such as by prior registration of the component 134 attached to the impactor) so that it can generate and display the image of the humeral trial component 134 on monitor 114 overlaid on the fluoroscopic image of the humerus 101. At any desired point in time, before, during or after the trial component 134 is properly placed on the humerus 101 to align with anatomical axis and according to proper orientation relative to other axes, the system can be instructed by foot pedal 110 or otherwise to begin tracking the position of the trial component 134 using the second navigational reference 104 attached to the humerus 101 rather than the one attached to the impactor 132. According to the preferred embodiment, the navigational sensor 100 "sees" at this point in time both the navigational references 104 on the impactor 132 and on the humerus 101 so that it already "knows" the position and orientation of the trial component 134 relative to the first navigational reference 104 on the impactor 132 and is thus able to calculate and store for later use the position and orientation of the trial component 134 relative to the second navigational reference 104 on the humerus 101. Once this "handoff" happens, the impactor 132 can be removed and the trial component 134 tracked with the navigational reference 104 on the humerus 101 as part of or moving in concert with the humerus 101. Similar handoff procedures may be used in any other instance as desired in accordance with the present invention.

FIG. 6 shows the placement of a humeral trial component 134 attached to humerus 101. The trial component 134 is attached via impactor 132. As explained above, both the humerus 101 and the impactor 132 have navigational references 104 attached that may be used in tracking and navigating trial component 134.

Figure 8:
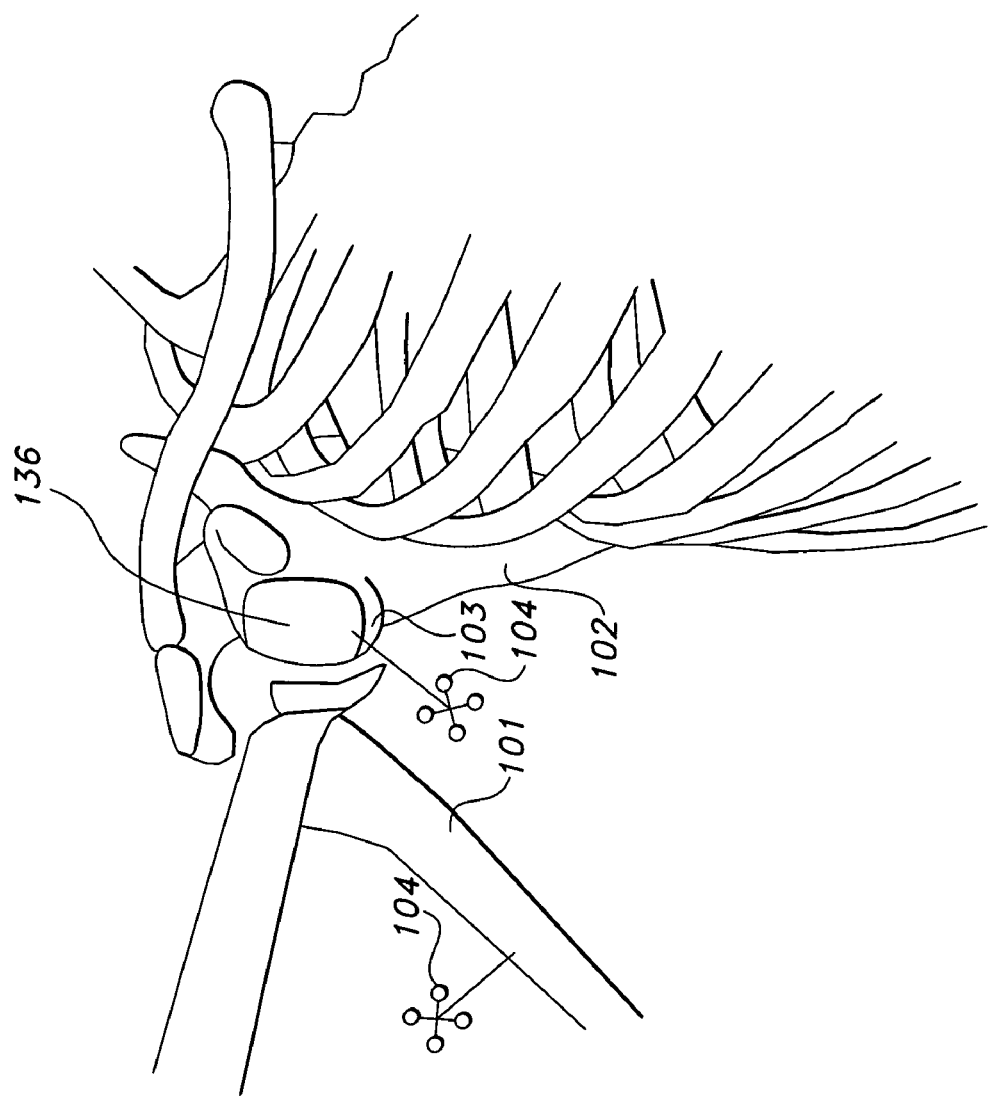
FIG. 8 shows navigation and placement of a glenoid trial component on a glenoid fossa according to some embodiments of the invention.

Similarly, as shown in FIG. 8, a glenoid trial component 136 can be placed on the glenoid 103 and then registered using a probe. A probe may be used to designate features on the glenoid trial component 136 of known coordinates, such as rotational alignment to the glenoid axis, the flexion/extension angle and the version/retroversion angle. As the probe is placed onto each feature, the system is prompted to save that coordinate position so that the system can match the glenoid trial component's 136 feature's coordinates to the saved coordinates. The system then tracks the glenoid trial component 136 relative to the anatomical reference frame.

The system may also indicate the fit of the glenoid keel or pegs within the glenoid before bone preparation is performed to insure that breakthrough to the posterior aspect of the scapula 102 does not occur.

FIG. 8 shows the placement of a glenoid trial component 136 attached to a glenoid 103.

Once the trial components are installed, the surgeon can assess alignment and stability of the components and the joint. During such assessment, in trial reduction, the computing can display on monitor 114 the relative motion between the trial components to allow the surgeon to make soft tissue releases and changes in order to improve the kinematics of the shoulder. The system can also apply rules and/or intelligence to make suggestions based on the information such as what soft tissue releases to make if the surgeon desires. The system can also display how the soft tissue releases are to be made.

During this assessment, the surgeon may conduct certain assessment processes such as external/internal rotation, rotary laxity testing, range of motion testing (external rotation, internal rotation and elevation) and stability testing (anterior, posterior and inferior translation). Thus, in the external/internal rotation test, the surgeon can position the humerus at the first location and press the foot pedal. He then positions the humerus at the second location and once again presses the foot pedal so that the computing functionality has registered and stored two locations in order to calculate and display the rotation and whether it is acceptable for the patient and the product involved. If not, the computer can apply rules in order to generate and display suggestions for releasing ligaments or other tissue, or using other component sizes or types. Once the proper tissue releases have been made, if necessary, and alignment and stability are acceptable as noted quantitatively on screen about all axes, the trial components may be removed and actual components navigated, installed, and assessed in performance in a manner similar to that in which the trial components were navigated, installed, and assessed.

At the end of the case, all alignment information can be saved for the patient file. This is of great assistance to the surgeon due to the fact that the outcome of implant positioning can be seen before any resectioning has been done on the bone.

The tracking and image information provided by systems and processes according to the present invention facilitate telemedical techniques, because they provide useful images for distribution to distant geographic locations where expert surgical or medical specialists may collaborate during surgery. Thus, systems and processes according to the present invention can be used in connection with computing functionality 108 which is networked or otherwise in communication with computing functionality in other locations, whether by PSTN, information exchange infrastructures such as packet switched networks including the Internet, or as otherwise desire. Such remote imaging may occur on computers, wireless devices, videoconferencing devices or in any other mode or on any other platform which is now or may in the future be capable of rending images or parts of them produced in accordance with the present invention. Parallel communication links such as switched or unswitched telephone call connections may also accompany or form part of such telemedical techniques. Distant databases such as online catalogs of implant suppliers or prosthetics buyers or distributors may form part of or be networked with computing functionality 108 to give the surgeon in real time access to additional options for implants which could be procured and used during the surgical operation.

The above methods and techniques are provided by way of example only, and other embodiments of the present invention can be used with other surgical location and preparation techniques and methods.

Changes and modifications, additions and deletions may be made to the structures and methods recited above and shown in the drawings without departing from the scope or spirit of the invention and the following claims.

What is claimed is:

1. A method for performing shoulder arthroplasty or hemi-arthroplasty surgical operations on portions of a shoulder joint, the method comprising:

generating navigational reference information relating to position and orientation of a body part forming at least a portion of the shoulder joint, wherein the body part is a humerus;

storing at least some of the navigational reference information in a computer;

attaching at least one first navigational reference capable of being tracked by the navigational sensor to the body part;

attaching at least one second navigational reference capable of being tracked by a navigational sensor to a surgical instrument;

receiving information from the navigational sensor regarding the position and orientation of the surgical instrument with respect to the body part, wherein the information received from the navigational sensor comprises the epicondylar axis of the humerus and the information received is used to determine the retroversion reference axis;

navigating the surgical instrument relative to the body part according to the position and orientation information;

tracking a trial component using the navigational sensor;

receiving information from the navigational sensor regarding the position and orientation of the trial component with respect to the body part;

generating and displaying on the monitor associated with the computer a visual image of the trial component properly positioned and oriented relative to the body part;

navigating the trial component relative to the body part and attaching the trial component to the body part according to the image;

performing soft tissue balancing tests while the navigation sensor continues to track the first and second navigational references;

using data generated by the computer to assess alignment and stability of the joint with the trial component attached; and releasing soft tissue to adjust alignment and stability.

2. The method of claim 1, wherein the surgical instrument comprises at least one of the following: a reamer, a resection guide, a cutting block and a probe.

3. The method of claim 1, wherein the information received from the navigational sensor comprises information regarding the anatomical axis of the humerus.

4. The method of claim 1, wherein the information received from the navigational sensor is used to determine an axis of the rotation for the shoulder joint.

5. The method of claim 1, further comprising:
modifying the body part using the surgical instrument; and
generating and displaying on a monitor associated with the computer information regarding the modification of the body part.

6. The method of claim 5, wherein the information displayed is used to determine the proper shoulder arthroplasty or hemiarthroplasty component size.

7. The method of claim 1, further comprising:
removing the trial component from the joint; and
navigating a prosthetic component using position and orientation information regarding the trial component.

8. The method of claim 7, wherein the prosthetic component comprises at least one of the following: a humeral component and a glenoid component.

9. The method of claim 1, wherein the navigational reference information is generated by an imager.

10. The method of claim 9, wherein the imager comprises one of the following:
a C-arm fluoroscope, a CT scanner, MRI equipment, ultrasound equipment, laser scanning equipment and a probe.

11. The method of claim 1, wherein the navigational reference information is one of the following: a resection plane, an anatomical axis, a mechanical axis, anterior/posterior reference plane, medial/lateral reference plane and rotational axis.

12. The method of claim 1, wherein the surgical instrument is a humeral reamer and the body part is a humerus and further comprising:
attaching a cutting block to the humeral reamer;
placing a surgical instrument through the cutting block into the humeral head; and
at least partially osteotomizing the humeral head.

13. A method for performing shoulder arthroplasty or hemiarthroplasty surgical operations on portions of a shoulder joint, the method comprising:
(a) attaching at least one first navigational reference capable of being tracked by a navigational sensor to a humerus forming at least a portion of the shoulder joint;
(b) generating navigational reference information relating to position and orientation of the humerus;
(c) storing at least some of the navigational reference information in a computer;
(d) tracking the position and orientation of the humerus as it moves;
(e) attaching at least one second navigational reference capable of being tracked by the navigational sensor to a humeral reamer;
(f) receiving information from the navigational sensor regarding the position and orientation of the humeral reamer with respect to the humerus;
(g) navigating the humeral reamer relative to the humerus according to the position and orientation information;
(h) attaching a cutting block to the humeral reamer;
(i) attaching at least one third navigational reference capable of being tracked by the navigational sensor to the cutting block;
(j) positioning the cutting block in at least one rotational degree of freedom through a range motion with infinite positions in the range; and at least one translational degree of freedom through a range of motion with infinite positions in the range; and
(k) receiving continuous information from the navigational sensor regarding the position and orientation of the cutting block with respect to the humerus or the humeral reamer, wherein the information comprises rotational information in at least one degree of freedom and translational information in at least one degree of freedom.

14. A method for performing shoulder arthroplasty or hemiarthroplasty surgical operations on portions of a shoulder joint, the method comprising:
obtaining data corresponding to a body part forming a portion of the shoulder joint using a first fiducial that is attached to the body part, wherein the first fiducial is capable of being tracked by at least one position and orientation sensor;
tracking the position and orientation of a surgical instrument relative to the body part using a computer that receives signals from the position and orientation sensor, wherein the surgical instrument is attached to a second fiducial capable of being tracked by the position and orientation sensor;
navigating the surgical instrument relative to the body part using the computer, which generates and displays on a monitor a visual representation of the position and orientation of the surgical instrument relative to the body part;
modifying the body part using the surgical instrument;
moving the body part to assess the shoulder joint as the computer tracks the position and orientation of the body part; wherein moving the body part to assess the shoulder joint comprises performing soft tissue balancing tests.

15. The method of claim 14, further comprising moving the body part as the computer tracks the position and orientation of an implant.

16. The method of claim 15, wherein moving the body part to assess the shoulder joint comprises assessing the alignment and stability of the shoulder joint with the implant attached to the shoulder joint.

17. The method of claim 16, further comprising releasing soft tissue to adjust alignment and stability of the shoulder joint.

18. The method of claim 14, wherein the surgical instrument comprises at least one of the following: a reamer, a resection guide, a cutting block and a probe.

19. The method of claim 14, wherein the body part is the humerus.

20. The method of claim 14, wherein the body part is the glenoid.

21. The method of claim 14, wherein the data corresponding to the body part comprises position and orientation information of the body part.

22. The method of claim 21, further comprising determining an axis of the rotation for the shoulder joint using the data corresponding to the body part.

23. The method of claim 14, wherein the data corresponding to the body part comprises information regarding the anatomical axis of the humerus.

24. The method of claim 14, wherein the data corresponding to the body part comprises information regarding at least one of a resection plane, an anterior reference plane, a posterior reference plane, a medial reference plane, or a lateral reference plane.

25. The method of claim 14, further comprising generating information regarding the modification of the body part using the computer.

26. The method of claim 25, wherein the information is used to determine a size for an implant to be attached to the shoulder joint.

* * * * *